(12) United States Patent
Raguram

(10) Patent No.: US 7,811,827 B2
(45) Date of Patent: *Oct. 12, 2010

(54) METHODS AND APPARATUS FOR CHARACTERIZING HEPARIN-LIKE GLYCOSAMINOGLYCAN MIXTURES

(75) Inventor: Sasisekharan Raguram, Hillsborough, NJ (US)

(73) Assignee: Momenta Pharmaceuticals, Inc., Cambridge, MA (US)

(*) Notice: Subject to any disclaimer, the term of this patent is extended or adjusted under 35 U.S.C. 154(b) by 105 days.

This patent is subject to a terminal disclaimer.

(21) Appl. No.: 12/166,292

(22) Filed: Jul. 1, 2008

(65) Prior Publication Data

US 2009/0043513 A1 Feb. 12, 2009

Related U.S. Application Data

(63) Continuation of application No. 10/931,939, filed on Sep. 1, 2004, now Pat. No. 7,407,810.

(60) Provisional application No. 60/500,745, filed on Sep. 4, 2003.

(51) Int. Cl.
*G01N 33/15* (2006.01)
*G01N 33/48* (2006.01)
*G01N 33/50* (2006.01)

(52) U.S. Cl. .................. 436/87; 436/71; 436/85; 436/86; 436/94; 700/268; 700/271; 702/19; 702/22; 702/27; 702/30

(58) Field of Classification Search ............. 436/85–87, 436/94; 700/266, 268, 271; 702/19, 22, 702/27, 30
See application file for complete search history.

(56) References Cited

U.S. PATENT DOCUMENTS

| 7,110,889 | B2 * | 9/2006 | Venkataraman et al. ....... 702/27 |
| 7,117,100 | B2 * | 10/2006 | Venkataraman et al. ....... 702/27 |
| 7,407,810 | B2 * | 8/2008 | Raguram ..................... 436/87 |
| 2002/0138480 | A1 * | 9/2002 | Wang et al. .................. 707/6 |
| 2002/0197610 | A1 * | 12/2002 | Schmitt et al. ................ 435/6 |

(Continued)

FOREIGN PATENT DOCUMENTS

WO 00/59627 * 10/2000

(Continued)

OTHER PUBLICATIONS

Seshadri et al., "Feature Extraction for Massive Data Mining," First International Conference on Knowledge Discovery & Data Mining, KDD-95:258-262 (1995).*

(Continued)

*Primary Examiner*—Arlen Soderquist
(74) *Attorney, Agent, or Firm*—Lando & Anastasi, LLP

(57) ABSTRACT

The invention provides methods and apparatus for characterizing complex polymeric mixture of interest. Candidate solutions are eliminated from a solution space using one or more experimental measurements of a polymeric mixture of interest. The elimination step can be repeated one or more times using different experimental measurements produced by various chemical and physical protocols, so that the remaining candidate solutions converge to describe the actual polymeric mixture under investigation. Once the composition of the complex polymeric mixture has been characterized, the information thus generated can be used to facilitate, for example, the manufacture of a bio-equivalent of the complex polymeric mixture.

39 Claims, 7 Drawing Sheets

U.S. PATENT DOCUMENTS

| | | | |
|---|---|---|---|
| 2003/0003456 A1* | 1/2003 | Schmitt et al. | 435/6 |
| 2003/0096281 A1* | 5/2003 | Venkataraman et al. | 435/6 |
| 2003/0191587 A1* | 10/2003 | Venkataraman et al. | 702/22 |
| 2003/0203385 A1* | 10/2003 | Venkataraman et al. | 435/6 |
| 2005/0244826 A1* | 11/2005 | Niehrs et al. | 435/6 |

FOREIGN PATENT DOCUMENTS

| | | | |
|---|---|---|---|
| WO | 02/12889 | * | 2/2002 |
| WO | 2005/111627 | * | 11/2005 |

OTHER PUBLICATIONS

Suda, Y. et al, Tetrahedron Letters 1996, 37, 1053-1056.*

Jayson, G. C. et al, British Journal of Cancer 1997, 75, 9-16.*

Gillet, V. J. et al, Journal of Chemical Information and Computer Sciences 1998, 38, 165-179.*

Zheng, W. et al, Journal of Chemical Information and Computer Sciences 1998, 38, 251-258.*

Cho, S. J. et al, Journal of Chemical Information and Computer Sciences 1998, 38, 259-268.*

Grassy, G. et al, Nature Biotechnology 1998, 16, 748-752.*

Dixon, S. L. et al, Journal of Chemical Information and Computer Sciences 1998, 38, 1192-1203.*

Ameer et al., "A New Approach to Regional Heparinization: Design and Development of a Novel Immobilized Heparinase Device," Blood Purification, 16-107-108 (1998).*

Lessel, U. F. et al, Journal of Chemical Information and Computer Sciences 2000, 40, 246-253.*

Polli, J. E. et al, Pharmaceutical Research 2001, 18, 734-741.*

Martin, Y. C. et al, Journal of Medicinal Chemistry 2002, 45, 4350-4358.*

Guerrini, et al., "A Novel Computational Approach to Integrate NMR Spectroscopy and Capillary Electrophoresis for Structure Assignment of Heparin and Heparan Sulfate Oligosaccharides," Glycobiology, 12:713-719 (2002).*

Pojasek, et al., "Complex Sugars as Emerging Therapeutic Targets," International Sugar Journal, 1243:306-312 (2002).*

Stepanchikova, A. V. et al, Current Medicinal Chemistry 2003, 10, 225-233.*

Shriver, et al., "Glycomics: A Pathway to a Class of New and Improved Therapeutics," Nature Reviews, 3:863-873 (2004).*

Sasisekharan et al., "Complex Carbohydrates, Molecules That Are Particularly Important for Communication Among Cells, Are Coming Under Systematic Study," American Scientist, 91:432-441 (2003).*

* cited by examiner

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Ile Thr Thr Gly Cys Ala Glu His Cys Ser Leu Asn Glu Asn Ile
  1               5                  10                  15

Thr Val Pro Asp
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gln Ala Leu Leu Val Asn Ser Ser Gln Pro Trp Glu Pro Leu Gln
  1               5                  10                  15

Leu His Val Asp Lys
            20
```

METHODS AND APPARATUS FOR CHARACTERIZING HEPARIN-LIKE GLYCOSAMINOGLYCAN MIXTURES

PRIOR APPLICATIONS

The present application is a continuation of (and claims priority to) U.S. Application Ser. No. 10/931,939, filed Sep. 1, 2004, which claims the benefit of U.S. Provisional Patent Application Ser. No. 60/500,745, filed Sep. 4, 2003, the contents of which are hereby incorporated by reference.

FIELD OF THE INVENTION

This invention relates generally to methods of characterizing polymeric mixtures. More particularly, in certain embodiments, the invention relates to methods of characterizing biopolymer mixtures.

BACKGROUND OF THE INVENTION

Over the years, it has been possible to characterize the composition of individual synthetic polymers of interest. This characterization usually has involved measuring the degree of polymerization, for example, measuring the number of particular primary units (building blocks), within a polymer of interest. This type of characterization may be adequate when the polymer is a synthetic polymer, for example, polyethylene, polypropylene, or the like, which exists as a mixture of individual polymer components made up of the same repeating unit (monomer), but having different degrees of polymerization. Because molecular weight reflects differences in the degree of polymerization, molecular weight alone may be sufficient to characterize polymeric mixtures made up of the same repeating units.

However, the characterization of complex polymeric mixtures, for example, polymeric mixtures in which each polymer may be made up of different building blocks, has proven to be far more difficult. Such mixtures occur in nature and can include, for example, mixtures of biopolymers in a sample of interest. For example, many therapeutically effective proteins are glycosylated with a diverse group of carbohydrates. Accordingly, these glycosylated proteins, also known as glycoproteins, exist as complex mixtures of proteins having different glycosylation patterns. As a result, molecular weight distribution alone usually cannot accurately describe batch-to-batch variations in different glycoprotein preparations or confirm that one glycoprotein preparation is the bio-equivalent of another glycoprotein preparation.

Sequencing methods have been developed for characterizing proteins (see, for example, "Biochemistry," Third Edition (1988), by Stryer, published by Freeman & Co., NY), nucleic acids (see, for example, Stryer (1988) supra), and polysaccharides (see, for example, U.S. Pat. No. 6,597,996 and U.S. Patent Application Publication No. US2003/0096281). However, these methods alone typically are insufficient to fully characterize each of the individual biopolymer species that are present in complex biopolymer mixtures. For example, the characterization of each of the polysaccharides in a complex mixture may require the isolation of each polysaccharide species present in the mixture prior to its sequencing using the methods described, for example, in U.S. Pat. No. 6,597,996. For many mixtures, species isolation can be impractical or even impossible. Even when the individual species present in a biological mixture can be physically isolated and characterized, the resulting characterization often does not provide insight into the active species within the mixture or the biological activity of the mixture.

Accordingly, the currently available methods for characterizing polymers are usually inadequate for characterizing complex biological mixtures. The need for new methods for characterizing complex biological mixtures is particularly evident in the pharmaceutical and biotechnology industries. For example, there are a variety of biologics—for example, glycoproteins such as interferon, erythropoietin, and the like; polysaccharides such as chondroitin sulfate, hyaluronan, heparin, and the like; and synthetic peptides such as copolymer 1, and the like—that have been approved by the U.S. Food and Drug Administration for use in humans. However, a complete characterization of each of the polymers within the biologic may be helpful so as to minimize batch-to-batch variations between different preparations of the biologic or to produce a bio-equivalent preparation of a biologic already approved for use in humans.

Accordingly, there is an ongoing need for methods capable of characterizing the composition of complex biological mixtures.

SUMMARY OF THE INVENTION

The invention is based, in part, upon the discovery of a method for characterizing the composition of a complex polymeric mixture. The method involves using experimental measurements to eliminate candidate solutions from an initial solution space in a step-wise manner until an acceptably small number of candidate solutions remain.

Analytical experiments can be performed to describe various attributes of a complex biological mixture. For example, mass spectroscopy can be performed to determine the molecular weight of various species in a mixture of interest. However, one type of measurement usually is insufficient to completely characterize a complex biological mixture. Therefore, under certain circumstances, it may be necessary to perform a number of different types of experiments, each producing very different types of data sets, to provide a complete characterization of the polymeric mixture.

The problem, however, becomes how to use these diverse data sets in order to obtain a full characterization of a mixture of interest. For example, it may be possible to model a complex mixture in terms of a set of measurable attributes, then solve the model using experimental measurements of the mixture of interest. However, a mathematical formulation of the problem may be intractable, due to the disparate types of data available, the lack of a fundamental mathematical model that adequately describes the mixture, and/or the complex interrelationship between the measurable attributes.

The invention overcomes this difficulty by providing a method of characterizing a complex biological mixture that avoids directly solving an integrated mathematical formulation of the problem. Instead, candidate solutions are evaluated to determine whether they provide an acceptable match of the value of an experimental measurement of the mixture of interest. Non-matching candidates are eliminated, and the method proceeds to the next experimental measurement until the candidate solution space is sufficiently narrowed.

Thus, in one aspect, the invention provides a method for characterizing a polymeric mixture. The method includes the steps of generating a solution space comprising a plurality of candidate solutions; providing an experimental measurement of a first attribute of a polymeric mixture of interest; determining for each of at least a subset of the candidate solutions a value of the first attribute; and characterizing the polymeric mixture by eliminating at least one of the candidate solutions from the solution space whose determined value does not correspond to the experimental measurement of the first attribute. The polymeric mixture may include, for example, one or more biopolymers, polysaccharides (linear and/or branched), monosaccharides, disaccharides, oligosaccharides, peptides, proteins, glycoproteins, nucleic acids, polynucleotides, lipids, lipopolysaccharides, and/or lipoproteins.

In one embodiment, the solution space contains candidate solutions that describe theoretically-possible polymeric mixtures whose components are made up of a known set of primary units. Each candidate solution is characterized by a quantity of components, and each component of a candidate solution is characterized by: (1) an abundance (for example, relative abundance) of the component in the candidate solution; (2) a composition defined by one or more members of the set of primary units; and (3) an arrangement of the one or more primary units in the component. For example, a candidate solution can be characterized by the number of polymeric species (components) in the mixture, the weight percent (or mole percent) of each polymeric species in the mixture, the molecular formula of each polymeric species in the mixture, and the sequence of primary units of each of the polymeric species in the mixture. In certain embodiments, the candidate solutions include components that are made up of arrangements of a set of primary units. The total number of primary units may be a number greater than 4, a number greater than 10, or a number greater than 20, for example. In other embodiments, there may be 4 or fewer primary units.

The method proceeds by obtaining or otherwise providing an experimental measurement of an attribute of a polymeric mixture to be characterized. The experimental measurement may be a physical or chemical measurement, for example, a spectrum of masses generated by mass spectroscopy. Then, the method involves determining values of the attribute for the mixtures represented by each of the candidate solutions using, for example, a mathematical model of the attribute, a set of rules and relationships, and/or database values. If the determined value of the attribute for a given candidate solution does not adequately correspond to the experimental measurement, the candidate solution is eliminated from the solution space. In one embodiment, the method continues eliminating candidates using different experimental measurements (for example, in a step-wise manner) to further narrow the set of candidate solutions until an acceptably small number of candidate solutions remain. The polymeric mixture can, therefore, be characterized using one or more of the remaining candidate solutions.

Steps to optimize performance of various methods of the invention include pruning the solution space based on rejected candidate solutions, ordering measurements prior to eliminating candidate solutions based on the type of information the measurements provide, and suggesting additional measurements based on a summary of the remaining solution space. These steps are discussed in more detail herein and may be performed singly or in combination.

In one embodiment, experimental measurements are ordered such that candidate solutions are eliminated on the basis of quantity of components, abundance of components, and/or composition of components before candidate solutions are eliminated on the basis of primary unit arrangement (for example, the sequence of the primary units). This provides for increased efficiency, for example, because a larger number of candidate solutions are eliminated from the solution space earlier in the procedure. In one embodiment, the ordering of experiments is suggested by a measure of difference between remaining candidate solutions.

The invention also provides a method of determining a measure of difference between two or more polymeric mixtures. The method includes the steps of ordering the components of each of the two or more mixtures to identify analogous components; evaluating a first metric that accounts for a difference between the number of components and their abundances in the mixtures; evaluating a second metric that accounts for a difference between the compositions of the components; and evaluating a third metric that accounts for a difference between the order of the primary units in components of the mixtures. The three metrics may be weighted according to their relative importance with respect to biological activity of the mixture, for example. The resulting measure of difference between mixtures may indicate a difference in biological activity, for example, and may be used to determine a level of ambiguity, or difference, between candidates remaining in a solution space after stepwise elimination, as discussed above. For example, the difference between mixtures remaining in a solution space in the candidate solution elimination procedure described above may be determined to be within a desired range or beneath a maximum level such that all remaining mixtures are biologically equivalent. In this way, for example, biologically equivalent variations of a pharmaceutical preparation comprising a plurality of biopolymers may be identified and used to produce a generic version of the pharmaceutical.

Methods of the invention can be used to characterize complex biologics for the manufacture of generic pharmaceutical preparations. The invention provides a method of characterizing a biological preparation. The method includes the steps of generating a solution space with candidate solutions, each of which is characterized by a quantity of components, wherein each component is characterized by an abundance of the component in the candidate solution, a composition of primary units, and an arrangement of the primary units; and characterizing a biological preparation at least in part by eliminating candidate solutions in a step-wise manner according to a comparison between an experimental measure of each of a plurality of attributes of the biological preparation and a value of the respective attribute determined for each of at least a subset of the remaining candidate solutions in the solution space. By way of example, the biological mixture may be a pharmaceutical preparation or a nutraceutical preparation.

Using this information, it is possible to produce a composition, for example, a generic version of a pharmaceutical preparation or nutraceutical preparation, that is defined by at least one of the remaining candidate solutions in the solution space. The method may also be used to further characterize the generic version of the pharmaceutical preparation by performing a step-wise candidate elimination procedure, as disclosed herein. Thus, methods of the invention may be used to de-convolute mixtures of biopolymers and to produce generic versions of biological preparations. The invention also includes the application of the candidate elimination procedure described herein to the design of manufacturing processes and quality control techniques for the production of a biologically active mixture.

BRIEF DESCRIPTION OF THE DRAWINGS

The objects and features of the invention may be better understood with reference to the drawings described below, and the claims. In the drawings, like numerals are used to indicate like parts throughout the various views.

DESCRIPTION OF THE ILLUSTRATIVE EMBODIMENT

Figure 1:
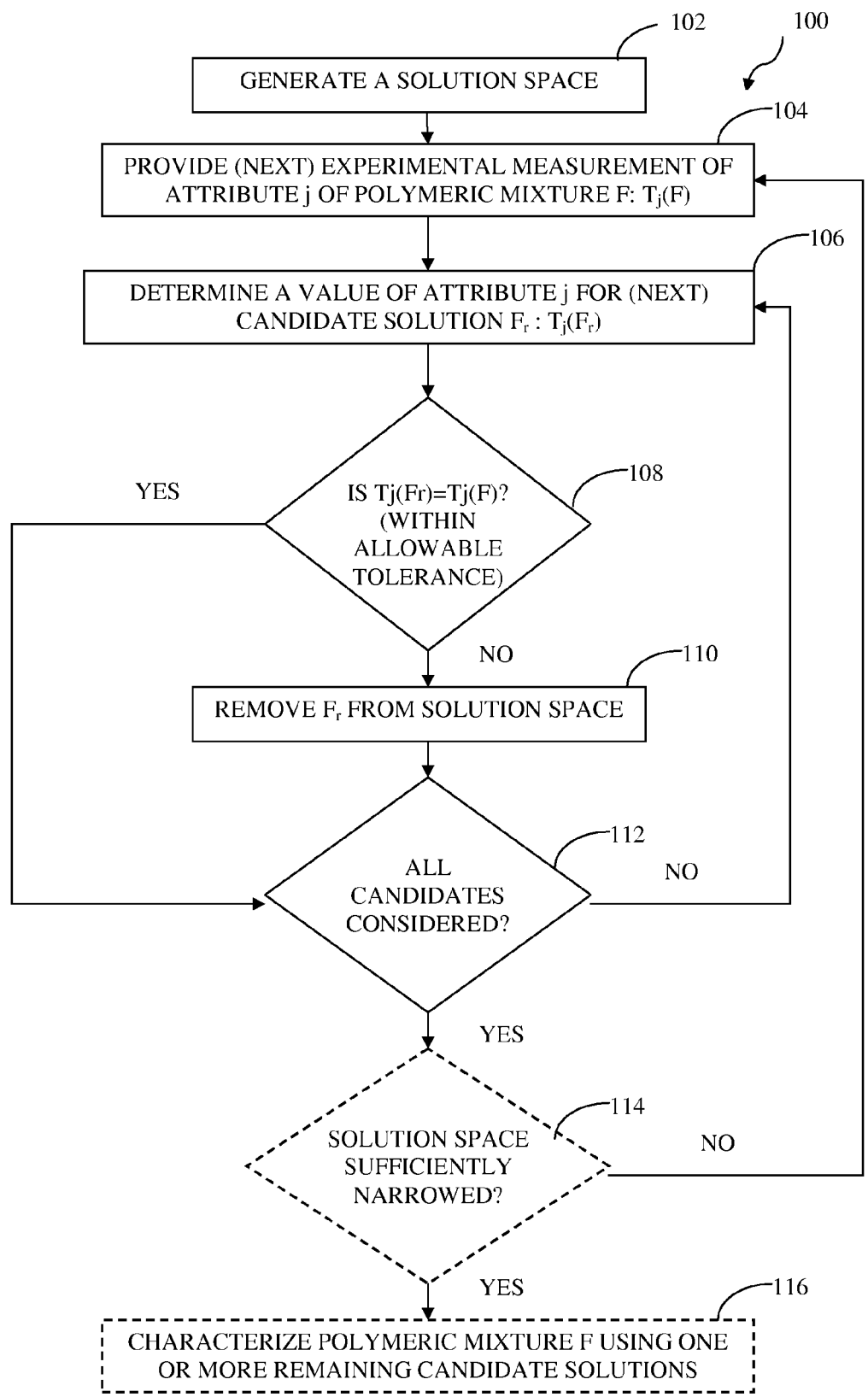
FIG. 1 is a block diagram showing steps in a method for characterizing a polymeric mixture from a set of candidate solutions, wherein analytical measurements are expressed as transformation functions, and wherein candidate solutions are eliminated in a step-wise procedure, according to an illustrative embodiment of the invention.

Throughout the description, where an apparatus is described as having, including, or comprising specific components, or where systems, processes, and methods are described as having, including, or comprising specific steps, it is contemplated that, additionally, there are apparati of the present invention that consist essentially of, or consist of, the recited components, and that there are systems, processes, and methods of the present invention that consist essentially of, or consist of, the recited steps.

It should be understood that the order of steps or order for performing certain actions is immaterial so long as the invention remains operable. Moreover, two or more steps or actions may be conducted simultaneously.

A computer hardware apparatus may be used in carrying out any of the methods described herein. The apparatus may include, for example, a general purpose computer, an embedded computer, a laptop or desktop computer, or any other type of computer that is capable of running software, issuing suitable control commands, receiving graphical user input, and/or recording information. The computer typically includes one or more central processing units for executing the instructions contained in software code that embraces one or more of the methods described herein. The software may include one or more modules recorded on machine-readable media, where the term machine-readable media encompasses software, hardwired logic, firmware, object code, and the like. Additionally, communication buses and I/O ports may be provided to link any or all of the hardware components together and permit communication with other computers and computer networks, including the internet, as desired.

Chemical nomenclature schemes used herein include HSGAG chemical structure notation, HSGAG hexadecimal notation, IUPAC carbohydrate nomenclature, and protein (amino acid) notation, as published by the International Union of Pure and Applied Chemistry, and the International Union of Biochemistry and Molecular Biology IUPAC-IUBMB Joing Commission on Biochemical Nomenclature (JCBN).

In general, the invention relates to a method of characterizing a complex polymeric mixture, for example, a complex biopolymer mixture, for example, a pharmaceutical or nutraceutical preparation. The method involves eliminating candidate solutions from a solution space based on how computed values of attributes of the mixtures represented by the candidate solutions compare to actual measurements of the attributes of a polymeric mixture of interest. The method can be used, therefore, to develop generic versions of pharmaceutical or nutraceutical preparations that contain a plurality of biopolymers. In addition, the method can be used to design a manufacturing process for providing uniform complex polymeric compositions by reducing or eliminating batch-to-batch variations.

The measurements of a polymeric mixture of interest are modeled as mathematical transformations which operate on a functional description of a mixture. Instead of solving for the functional description by determining inverse transforms, methods of the invention generate a solution space of theoretically-possible mixtures made up of components having a known set of primary units (for example, monomeric building blocks), and then compute values of measurements for mixtures characterized by the candidate solutions. For each experimental measurement, the candidates whose computed values do not match the measured value within an allowable tolerance are eliminated. Remaining candidates are eliminated in a stepwise manner by considering how their computed values compare to the measured attributes of the polymeric mixture. The procedure is best performed by computer, since the solution space in early iterations may contain a very large number of candidates for certain applications, for example, an initial solution space may contain on the order of $10^{20}$, $10^{25}$, or more candidate solutions.

The invention methods provide a means of integrating disparate types of experimental data to provide a characterization of a polymeric mixture. The experimental measurements may include, for example, a single or combination of physical and/or chemical measurements. Useful experimental measurements may be derived from a variety of different techniques, including, for example, (i) electrophoretic techniques, for example, capillary electrophoresis, one-dimensional (1D) gel electrophoresis, two-dimensional (2D) gel electrophoresis, (ii) spectroscopic techniques, including, for example, light spectroscopy, mass spectroscopy, Fourier transform infrared spectroscopy, (iii) resonance based approaches including, for example, nuclear magnetic resonance (NMR), for example, 1D-NMR and 2D-NMR, resonance Raman, electron paramagnetic resonance, (iv) binding techniques, for example, protein and/or carbohydrate binding assays, and (v) bioassays, including, for example, enzyme activity and/or inhibition assays. Measurements provide information about the number of different polymeric (for example, oligomeric) components in the mixture, the relative abundance of each component, the content or composition of each component, and/or the order in which the primary units (building blocks) are arranged in each component.

Other steps to optimize performance of various methods of the invention include pruning the solution space based on rejected candidate solutions, ordering measurements prior to eliminating candidate solutions based on the type of information the measurements provide, and suggesting additional measurements based on a summary of the remaining solution space. These steps are discussed in more detail below and may be performed singly or in combination.

Important classes of biological macromolecules include nucleic acids, for example DNA and RNA, proteins, peptides, carbohydrates, glycans (linear and branched), lipids, glycoproteins, lipoproteins, proteoglycans, and glycolipids. Mixtures of biological macromolecules are commonly observed in physiological situations as well as those involving their biochemical characterization. Physiologically relevant mixtures of biological macromolecules arise from protein-protein associations and multivalent protein-ligand interactions. An example of a complex biological mixture is a mixture containing proteins. Another important example of biological mixtures is a mixture of complex carbohydrates or glycans that are isolated from tissues and/or cells. Glycans can be linear polymers of repeating pyranose monosaccharide rings or branched structures based on multiple linkages between the monosaccharide rings. Depending on the type of linkages and exocyclic substitutions of the monosaccharides, there are several families of carbohydrates. With growing awareness of the important biological roles of glycans and with the development of novel carbohydrate based therapeutics, it is becoming necessary to characterize glycan mixtures in order to correlate specific properties of the mixture to their biological role or clinical response. Complex biologics is a term for complex mixture of biopolymers, especially in the context of therapeutics.

Heparin-like glycosaminoglycans (HSGAGs) are linear polysaccharides containing a disaccharide repeat unit. HSGAGs may be represented by the formula $(U_{2X}-H_{NY, 3X, 6X})_n$, where U is uronic acid, H is glucosamine, and the subscripts indicate certain variations. Each disaccharide unit can have the following variations: the uronic acid, U, can be one of two types—Iduronic (I) or Glucuronic (G); the 2X position of the uronic acid (I or G) can be sulfated (2S) or not sulfated (no subscript); the NY position of glucosamine (H) can be sulfated (NS), acetylated (NAc) or neither (NH2); the 3X position of H can be sulfated (3S) or not sulfated (no subscript); and the 6X position of H can be sulfated (6S) or not sulfated (no subscript). These variations give rise to 48 theoretically possible disaccharide units. However, at present, only 50% of these theoretically possible units have actually been observed in nature.

Examples of disaccharide repeat units include the following: $I_{2S}-H_{NS,6S}$ represents a disaccharide containing iduronic acid linked to glucosamine and sulfated at the 2X, NY and 6X positions; $G-H_{NAc,6S}$ represents a disaccharide containing glucuronic acid linked to glucosamine and acetylated at the NY position and sulfated at the 6X position; and $I-H_{NH2,6S}$ represents a disaccharide containing iduronic acid linked to glucosamine and having a free (neither acetylated nor sulfated) NY position and sulfated at the 6X position.

Another chemical modification to the disaccharide unit of an HSGAG is designated by "ΔU", which indicates a uronic acid unit that is derived from iduronic or glucuronic acid after an H-I or H-G linkage is formed as a result of heparinase cleavage. It is hard to determine whether the ΔU was derived from I or G. ΔU always occurs on the left (non-reducing end of a sequence), for example, it does not occur internally. A further chemical modification to the disaccharide unit of an HSGAG is designated by "Manito", which indicates a special unit derived from a glucosamine that is sulfated at the NY position ($H_{NS}$) after a $H_{NS}$-I or $H_{NS}$-G linkage is cleaved by nitrous acid treatment. This unit is chemically different from the parent glucosamine it was derived from. Depending on the chemical procedure used, it is possible to determine the identity of the parent glucosamine (for example, variations at the 6X, 3X and NY position) given the identity of the mannitol unit.

A complete characterization of a complex mixture of biopolymers, for example, an HSGAG mixture, is accomplished by identifying the following: the number of unique molecules (components) in the mixture and the abundance of each component; the composition—that is, the monomer units, or primary units—of each of the unique components; and the order (sequence) in which the primary units are arranged in each component. Identification of the arrangement of primary units in each component may also include determining the branching structure of a given component if the component is not linear. Tables 1 and 2 show illustrative representations of two polysaccharide mixtures—one containing linear components, and the other containing branched components. In these examples, the following primary units are found: Gal, Man, GalNAc, GlcNAc, NeuAc, and NeuGc.

TABLE 1

Representation of a polysaccharide mixture made up of linear components

| # | Formula | Relative Abundance (%) |
|---|---|---|
| 1 | I-HNAc,6S G-HNS,3S,6S I2S-HNS,6S I2S-HNS,6S | 9.0 |
| 2 | I-HNAc,6S G-HNS,3S,6S I2S-HNS I2S-HNS,6S | 17.2 |
| 3 | I2S-HNS,6S G-HNS,6S I2S-HNS,6S I2S-HNS,6S | 24.2 |
| 4 | I2S-HNS,6S I2S-HNS,6S I2S-HNS,6S I2S-HNS,6S | 32.4 |
| 5 | I-HNAc,6S G-HNS,6S I2S-HNS I2S-HNS,6S | 17.2 |

TABLE 2

Representation of a polysaccharide mixture made up of branched components

| Glycoform | Relative Abund. (%) | Sequence |
|---|---|---|
| G1 | 20.0 | Galb4GlcNAcb2Mana3(GlcNAcb2Mana6)(GlcNAcb4)Manb4GlcNAcb4(Fuca6)GlcNAc |
| G2 | 10.5 | Fuca3(Galb4)GlcNAcb2Mana3(Mana6)Manb4GlcNAcb4(Fuca6)GlcNAc |
| G3 | 21.5 | Galb4GlcNAcb2Mana3(GlcNAcb2Mana6)Manb4GlcNAcb4(Fuca6)GlcNAc |
| G4 | 45.2 | GlcNAcb2Mana3(Mana6)Manb4GlcNAcb4(Fuca6)GlcNAc |
| G5 | 2.8 | Galb4GlcNAcb2Mana3(Mana6)Manb4GlcNAcb4(Fuca6)GlcNAc |

Different types of measurements are needed in order to characterize a biopolymer mixture. The different types of measurements typically generate very different types of data sets. Each of the measurements describe a specific subset of the measurable attributes, or properties, of the mixture.

For example, measurements that contain information about components, linkages between primary units of components, and relative abundances of primary units can be used to characterize a biopolymer mixture. The information from the physical measurements does not have to be complete; it can be partial. Most practical physical measurement techniques provide only partial information about a biopolymer mixture. In one embodiment of the invention, different pieces of partial information are integrated to provide complete characterization. For example, a combination of two or more of the following measurements of a polysaccharide mixture of interest can be obtained for characterization of the mixture: capillary electrophoresis; 1D NMR; 2D NMR; matrix assisted laser desorption ionization mass spectrometry (MALDI-MS); carbohydrate protein binding level analysis; chromatographic analysis (UV) alone or combined with light scattering and/or SEC; and measurements made following enzyme-based cutting and/or desulfation.

For the case of HSGAG mixtures, capillary electrophoresis (CE) can be performed as part of a compositional analysis. The mixture is treated for an extended period of time with heparinases such that all the linkages are cleaved. The enzymes break the mixture down into the disaccharide primary units (building blocks). All the disaccharide units will be of the form $\Delta U_{2X}-H_{NY,3X,6X}$ where the $\Delta U$ is formed as a result of heparinase cleavage. Therefore, it will be difficult or impossible to determine whether the $\Delta U$ was derived from Iduronic or Glucuronic acid. However the presence of the $\Delta U$ makes the disaccharide unit detectable because of its absorbance at 232 nm. CE is a sensitive procedure that can distinguish positional modifications on disaccharide units. For example, a $\Delta U_{2S}-H_{NS}$ and a $\Delta U-H_{NS,6S}$ will migrate at different times giving two unique peaks, although the number of sulfates is the same on both these units. The identity of the disaccharide unit is confirmed by analyzing known disaccharide standards, available for most of the $\Delta U$-containing disaccharides, and comparing the migration time of the detected peaks between the known and the standard. Integration of these peaks gives the relative molar abundance of each disaccharide unit. The molar abundance can be converted into molar percentage abundance.

Capillary electrophoresis experimental protocols are described for mixtures of heparin-like glycosaminoglycans (HSGAGs), for example, in the following publications: (1) Rhomberg et al. (1998), "Mass spectrometric and capillary electrophoretic investigation of the enzymatic degradation of heparin-like glycosaminoglycans," *Proc Natl Acad Sci USA* 95, 4176-81; (2) Venkataraman et al. (1999), "Sequencing complex polysaccharides," *Science* 286, 537-42; and (3) Shriver et al. (2000), "Sequencing of 3-O sulfate containing heparin decasaccharides with a partial antithrombin III binding site. *Proc Natl Acad Sci USA* 97, 10359-64.

MALDI mass spectroscopy of an HSGAG can provide an accurate mass of a parent n-mer. The technique can accurately determine the mass of oligosaccharides up to 7-mer. Very low mass ranges, for example, disaccharides with one or no sulfate groups, are difficult to detect. Because of the nature of the variations in the disaccharide and the accuracy of the MALDI-MS method (<1 mass unit), it is possible to uniquely determine the length, number of sulfates, and number of acetates for n-mers up to 7-mers. Beyond 7-mers, the difference in masses are smaller than the accuracy of the MALDI-MS methodology. Treatment of a parent n-mer with an enzyme will give a mass profile of the shorter fragments formed by breaking down the parent. Since shorter fragments are mostly smaller than 7-mers, it is possible to uniquely determine their length, sulfates, and acetates from their masses. Performing the MALDI-MS procedure on any n-mer does not generally give information on which positions are sulfated or acetylated, nor does it tell how many iduronic and glucuronic acids there are in the n-mer. However, parts of this information can be obtained based on analyzing the mass profiles and applying the rules that govern the specificity and the time-dependent mechanism of the break-down of the n-mer by enzymatic (stronger rules) or chemical (weaker rules) methods. Unlike CE, MALDI-MS is not completely quantitative. Accordingly, it can be difficult to estimate the abundance of the species represented by a peak based solely on the intensity or integration of the mass peak.

Matrix assisted laser desorption ionization mass spectrometry (MALDI-MS) of HSGAG mixtures is described, for example, in the following publications: (1) Rhomberg et al. (1998), "Mass spectrometric and capillary electrophoretic investigation of the enzymatic degradation of heparin-like glycosaminoglycans," *Proc Natl Acad Sci USA* 95, 4176-81; (2) Rhomberg et al. (1998), "Mass spectrometric evidence for the enzymatic mechanism of the depolymerization of heparin-like glycosaminoglycans by heparinase II," *Proc Natl Acad Sci USA* 95, 12232-7; (3) Ernst et al. (1998), "Direct evidence for a predominantly exolytic processive mechanism for depolymerization of heparin-like glycosaminoglycans by heparinase I," *Proc Natl Acad Sci USA* 95, 4182-7; (4) Juhasz and Biemann (1994), "Mass spectrometric molecular-weight determination of highly acidic compounds of biological significance via their complexes with basic polypeptides," *Proc Natl Acad Sci USA* 91, 4333-7; and (5) Juhasz, P. and Biemann, K. (1995), "Utility of non-covalent complexes in the matrix-assisted laser desorption ionization mass spectrometry of heparin-derived oligosaccharides," *Carbohydr Res* 270, 131-47.

Analysis of a parent n-mer can be performed without enzymatic digest via nuclear magnetic resonance (NMR) analysis. 1D and/or 2D NMR analysis provides the percentage abundance of individual monosaccharide units, particularly $I_{2S}$, IG, $H_{NAc,6X}$, and $H_{NS,3X,6X}$. Sulfation at the 6-O position cannot be fully assigned via NMR analysis. NMR analysis provides quantitative information of iduronic versus glucuronic acid content in a given n-mer. In addition, NMR analysis also provides information about linkages between the H of one primary unit and the U of the adjacent primary units. For example, if the parent n-mer, $[I_{2S}-H_{NS,6S}]-[G-H_{NS,6S}]-[I_{2S}-H_{NS}]-[I-H_{NAc,6S}]-[G-H_{NS}]$ is analyzed using NMR, then the information shown in Table 3 can be obtained. The "Relative Abundance" column in Table 3 indicates the number of disaccharide units (primary units, building blocks) of the parent n-mer that contain the given monosaccharide or linkage. The "Percentage Abundance" column in Table 3 indicates the percentage of disaccharide units containing the listed monosaccharide or containing the linkage shown.

TABLE 3

Example of information obtained from NMR measurement

| | Relative Abundance | Percentage Abundance |
|---|---|---|
| Monosaccharide | | |
| $I_{2S}$ | 2 | 40 |
| I | 1 | 20 |
| G | 2 | 40 |
| $H_{NS,6X}$ | 4 | 80 |
| $H_{NAc,6X}$ | 1 | 20 |
| Linkages | | |
| $H_{NS,6X}$-$I_{2X}$ | 2 | 50 |
| $H_{NS,6X}$-G | 1 | 25 |
| $H_{NAc,6X}$-G | 1 | 25 |

1D-NMR and 2D-NMR of HSGAG mixtures are described, for example, in the following publications: (1) Casu et al. (1996), "Characterization of sulfation patterns of beef and pig mucosal heparins by nuclear magnetic resonance spectroscopy," *Arzneimittelforschung* 46, 472-7; (2) Guerrini et al. (2002), "A novel computational approach to integrate NMR spectroscopy and capillary electrophoresis for structure assignment of heparin and heparan sulfate oligosaccharides," *Glycobiology* 12, 713-9; (3) Guerrini et al. (2001), "Combined quantitative 1H and 13C-NMR spectroscopy for characterization of heparin preparations," *Semin Thromb Hemost* 274, 100-123; (4) Mulloy, B. (1996), "High-field NMR as a technique for the determination of polysaccharide structures," *Mol Biotechnol* 6, 241-65; (5) Mulloy and Johnson (1987), "Assignment of the 1H-NMR spectra of heparin and heparan sulphate," *Carbohydr Res* 170, 151-65; and (6) Torri et al. (1985), "Mono- and bidimensional 500 MHz 1H-NMR spectra of a synthetic pentasaccharide corresponding to the binding sequence of heparin to antithrombin-III: evidence for conformational peculiarity of the sulfated iduronate residue," *Biochem Biophys Res Commun* 128, 134-40.

An HSGAG polymer can be depolymerized using chemical and/or enzymatic methods. At least 3 different enzymes (see below) are known to cleave HSGAG polymers between the glucosamine and the next uronic acid (H-U linkage), and the specificity and mechanism of cleavage of these enzymes are reasonably well characterized. For example, Heparinase I is an enzyme that preferentially cleaves "–$H_{NS,3X,6X}$–$I_{2S}$–" to yield "–$H_{NS,3X,6X}$" and "($\Delta U_{2S}$–", where $\Delta U_{2S}$ is a special uronic acid derived from $I_{2S}$ in this case. Although $\Delta U_{2S}$ can also be derived from $G_{2S}$, it has been found that $H_{NS,3X,6X}$-$G_{2S}$ linkages typically are ss preferred by heparinase I. Accordingly, although it is unlikely, it cannot be completely ruled out that $G_{2S}$ is the source of $\Delta U_{2S}$ Heparinase III is an enzyme that cleaves "–$H_{NS/Ac,6X}$–G/I–". Heparinase III preferably cleaves G-containing linkages over I-containing linkages; however, rules for this enzyme are not as strongly defined as heparinase I. Heparinase II is an enzyme that cleaves both heparinase I and heparinase III-cleavable linkages. This enzyme is also not as extensively characterized as heparinase I.

In addition to heparinases, other enzymes called exo-enzymes specifically remove sulfate and acetate groups from their corresponding positions in each disaccharide unit. For example, the 2-O sulfatase specifically removes the sulfate at the 2X position of the $\Delta U_{2S}$-containing disaccharide unit at the left (non-reducing) end. Less is known in terms of the specificity and activity of these enzymes for their application as tools in sequencing.

While enzymatic methods for breaking down a HSGAG chain are highly specific and regulated, chemical methods are more non-specific and random. One chemical method that can be used to break down HSGAG polymers is treatment with nitrous acid. Nitrous acid randomly cleaves –$H_{NS,3X,6X}$–$U_{2X}$– to yield "–$Man_{3X,6X}$" and "($U_{2X}$–", where Man is a special unit derived from the parent H-containing unit. Unlike heparinases, nitrous acid treatment does not convert Iduronic acid or Glucuronic acid into $\Delta U$, so the identity of the uronic acid is retained.

Enzymatic digest of HSGAGs is described, for example, in the following publications: (1) Ernst et al. (1995), "Enzymatic degradation of glycosaminoglycans," *Crit Rev Biochem Mol Biol* 30, 387-444; (2) Ernst et al. (1998), "Direct evidence for a predominantly exolytic processive mechanism for depolymerization of heparin-like glycosaminoglycans by heparinase I," *Proc Natl Acad Sci USA* 95, 4182-7; (3) Shriver et al. (2000), "Cleavage of the antithrombin III binding site in heparin by heparinases and its implication in the generation of low molecular weight heparin," *Proc Natl Acad Sci USA* 97, 10365-70; and (4) Rhomberg et al. (1998), "Mass spectrometric evidence for the enzymatic mechanism of the depolymerization of heparin-like glycosaminoglycans by heparinase II," *Proc Natl Acad Sci USA* 95, 12232-7.

Thus, the problem of characterizing a biopolymer mixture may be viewed as the integration of diverse data sets to obtain a solution characterization. The problem can be expressed as follows. Consider a polymer mixture containing components made up of a set of primary units $\{z_1, z_2, z_3, \ldots, z_n\}$. Let $F\{s\}$ represent a set of functions that characterize the polymer mixture. Relate a primary unit z to an array $S(x,y)$ representing components of the polymer mixture according to Equation 1:

$$z = S(x,y) \quad (1)$$

where z belongs to the set of primary units $\{z_1, z_2, z_3, \ldots, z_n\}$ and x and y are integers; x denotes the component number and y denotes the position in the component. In one embodiment, an element in set z can either be a primary unit or a link between primary units, for example, in the case of mixture with branched polymer components. Next, express a relative abundance, a, of a component according to Equation 2 as follows:

$$a = A(x) \quad (2)$$

where x denotes the component number and a is the relative abundance.

Define $R_a, R_b, R_c, \ldots, R_n$, to express relationships and/or rules with respect to the elements z. For example, let $R_a(Z)=m$ be a relationship that expresses the mass m due to the presence of element z in a given mixture. The different experimental measurements used in characterizing a mixture can be defined as transformation functions $T_a, T_b, T_c, \ldots T_n$, operating on a set of functions, $F\{s\}$. For example, $T_a(F\{s\})$ represents a specific transformation of function set $F\{s\}$ that would provide a value obtained from an experimental measurement of the mixture. A goal of the method of characterizing the mixture is to reconstruct function set $F\{s\}$ given the transforms $T_a(F\{s\}), T_b(F\{s\}), \ldots, T_n(F\{s\})$ and relationships $R_a, R_b, R_c, \ldots R_n$.

For each transform $T_i$, there exist multiple functions $F_k\{S\}$ such that Equation 3 holds to within an acceptable tolerance:

$$T_i(F_k\{s\})=T_i(F\{s\}) \quad (3)$$

The method involves selecting an initial transform, $T_i$, from the set of transforms available (for example, experimental measurements) and generating an initial solution space. The initial solution space is the set of all functions $F_k$ that satisfy the expression $T_i(F_k)=T_i(F)$ to within an acceptable tolerance. The size of the solution space is reduced by removing candidate solutions that do not satisfy all of the other transformation relationships that exist. The resultant solution space represents the family of candidate solutions that cannot be further discriminated using the experimental data currently available.

Thus, for each of the transforms $T_j$ that belong the set of transforms $\{T_a, \ldots, T_n\}$ other than the transform used to generate the initial solution space, the method proceeds by computing $T_j(F_r)$ for elements in the solution space, $F_r$. The method then removes $F_r$ from the solution space if $T_j(F_r)$ is not equal to $T_j(F)$ to within an acceptable tolerance. The candidate solutions that remain in the solution space after all the transforms/experimental measurements have been considered constitute all the possible solutions that satisfy the existing measurements.

Methods can be employed to prune the solution space without inspecting each and every element of the solution space. These methods can significantly speed up convergence to a solution. For example, the number of elements in an initial solution space can be on the order of $10^{10}$, $10^{20}$, $10^{25}$, or greater and, therefore, it can be inefficient to compute $T_j(F_r)$ for this quantity of candidate solutions. Methods of pruning the solution space are domain-specific and incorporate knowledge about the transformations (physical measurements) being performed. Exemplary pruning methods are discussed elsewhere herein in more detail.

The invention may be more readily understood by reference to FIG. 1, which is a block diagram showing steps in a solution candidate elimination procedure, according to one embodiment of the invention. Dashed lines in FIG. 1 indicate optional steps. A solution space is generated in step 102, which includes theoretically-possible combinations of a known set of primary units to form polymeric components of mixture. The solution space typically contains candidates with varying numbers of components, where each candidate's components may have different compositions and different arrangements of primary units. In early iterations, for some applications, there may be upwards of about $10^{10}$, $10^{20}$, $10^{25}$, or more candidate solutions in the solution space.

In one embodiment, a mass spectroscopy measurement can be used to generate the initial solution space. For illustrative purposes, an exemplary spectroscopy measurement is presented in Table 4 for illustrative purposes.

TABLE 4

Example mass spectroscopy measurement

| Mass (Daltons) | Relative abundance |
|---|---|
| 1000 | 40 |
| 1500 | 60 |

With this data in hand, all combinations of building blocks (primary units) that satisfy the mass spectroscopy measurement are determined. In the simplified example of Table 4, the initial solution space is made up of all mixtures with components whose primary unit masses sum to either 1000 Daltons or 1500 Daltons. For sake of illustration, one possible combination of primary unit masses add up to 1000 Daltons—for example, the combination of primary units M and N—and two possible combinations of primary unit masses add up to 1500—for example, the combination D, D, and N, and the combination D, D, and R. Accordingly, the total number of components that make up mixtures in this illustration will be either 2 or 3.

Table 5 lists a small subset of the candidates in the initial solution space in the illustrative example described above. Table 5 shows candidate solutions S1, S2, S3, and S4, each having either two or three components, as shown. All other possible combinations of the two components DND and DDR in which the abundance of the two components add up to 60 will also be candidates in the initial solution space. Furthermore, all arrangements of the primary units within each of the three possible components are also candidates in the solution space.

TABLE 5

Example subset of initial candidate solution space based on the mass spectroscopy measurement of Table 4

| | S1 | | S2 | | S3 | | S4 | |
|---|---|---|---|---|---|---|---|---|
| | Sequence | Rel. Abund. | Sequence | Rel. Abund. | Sequence | Rel. Abund. | Sequence | Rel. Abund. |
| 1 | MN | 40 | MN | 40 | MN | 40 | MN | 40 |
| 2 | DND | 60 | DDR | 1 | DDR | 60 | DDN | 60 |
| 3 | | | DND | 59 | | | | |

In step 104 of FIG. 1, an experimental measurement, $T_j(F)$, of attribute j of a polymeric mixture of interest (F) is provided. The experimental measurement may include, for example, a single or combination of physical and/or chemical measurements, as discussed elsewhere herein. In step 106, a value of the attribute is calculated for a candidate solution $F_r$ based on a model and/or based on database values. Then, the calculated value is compared to the measured value in step 108. If the values are not equal (within a given tolerance), the candidate solution $F_r$ is removed from the solution space in step 110; otherwise, the candidate stays in the solution space. By way of example, the value of the tolerance may be a root-mean-square (RMS) error indicated by Equation 4 as follows:

$$\text{Tolerance}=\text{sqrt}(\Sigma[T_j(F_r(k))-T_j(F(k))]^2) \quad (4)$$

where the sum is performed over all measurement values k that are determined for the candidate solutions.

To illustrate steps 104, 106, and 108, consider a linear polymer mixture containing the primary units $\{z1, z2, z3, \ldots, z_n, \ldots, z_{2n}\}$, wherein Equations 1 and 2 apply. In this illustrative example, the experimental measurement, $T_j(F)$, is a capillary electrophoresis measurement. A relationship, or model, that predicts a capillary electrophoresis measurement for a linear polysaccharide mixture is represented by Equation 5 as follows:

$$r = CE(c) \quad (5)$$

where c belongs to the set $\{c_1, c_2, c_3, \ldots, c_n\}$; $c_i$ contains the elements (building blocks, primary units) $z_{2i-1}$ and $z_{2i}$; and r is the relative abundance of the elements belonging to the set $\{c_1, c_2, c_3, \ldots, c_n\}$. The transformation that represents the capillary electrophoresis measurement of the polymeric mixture of interest can be written according to Equation 6:

$$T_j(F\{s\}) = CE(c_k) = \Sigma[A(i) * \{\text{Count}(i, 2*k-1) + \text{Count}(i, 2*k)\}/\text{TotalCount}(i)] \quad (6)$$

where Count(i,j) is the number of elements $z_j$ found in component i; and TotalCount(i) is the number of elements in component i. Assume that Table 6 then represents a candidate solution $F_r$ in the solution space.

TABLE 6

Example candidate solution
S1

|   | Sequence | Rel. Abund. |
|---|----------|-------------|
| 1 | MN       | 40          |
| 2 | DDR      | 1           |
| 3 | DND      | 59          |

In step 106 of FIG. 1, a value of the attribute (for example, compositional information provided by capillary electrophoresis measurement) is determined for the candidate solution shown in Table 6. For this candidate solution, using Equations 1 and 2, it can be determined that A(1)=40; A(2)=1; A(3)=59; S(1,1)=M; S(1,2)=N; S(2,1)=D; S(2,2)=D; S(2,3)=R; S(3,1)=D; S(3,2)=N; and S(3,3)=D. The transformation of Equation 6 can be applied, and the resulting value of the capillary electrophoresis attribute can be obtained for the candidate solution of Table 6. Thus, for this candidate solution, CE(C1)=0, C1={A, B}; CE(C2)=(2*(0.01)+2*(0.59))/3=40%; C2={C,D}; and so on. In step 108 of the method of FIG. 1, the resultant value of the transformation function CE is compared with the actual CE measurement of the mixture of interest to determine if they are the same, within an allowable tolerance. If not, the candidate solution is removed from the solution space.

Other experimental measurements that can be used include, for example, a 1-D NMR measurement, a 2-D NMR measurement, and measurements following enzyme digestion. For example, a 1-D NMR measurement for an HSGAG mixture provides the monosaccharide composition and can be expressed as in Equation 7:

$$Am = \text{MonoSac}(ms) \quad (7)$$

where Am is the relative abundance of the monosaccharide and ms belongs to the set of monosaccharide units $\{ms_1, ms_2, ms_3, \ldots, ms_n\}$. Transformation T, which represents the function MonoSac, can be expressed as in Equation 8:

$$T(F\{s\}) = \text{MonoSac}(ms_k) = \Sigma[A(i) * \{MSCount(i,k)/\text{Total}MSCount(i)\}] \quad (8)$$

where the sum is calculated over all components; TotalMSCount(i) is the number of monosaccharides in component I; and MSCount(i,j) is the number of elements $z_j$ found in component i that contains monosaccharide $ms_j$. In other words, MSCount(i,j) is the number of elements $z_j$ containing the monosaccharide $ms_j$ found in S(x,y) where x=i and y can take on all possible values.

A 2-D NMR measurement for a HSGAG mixture provides relative abundance of the links between the disaccharide units and can be expressed as in Equation 9:

$$A1 = \text{DiSacLink}(\text{link}) \quad (9)$$

where "link" belongs to the set of links between the disaccharide units $\{\text{link}_1, \text{link}_2, \text{link}_3, \ldots, \text{link}_n\}$; and A1 is the relative abundance. Transformation T that represents the function DiSacLink can be expressed as in Equation 10:

$$T(F\{s\}) = \text{DiSacLink}(\text{link}_k) = \Sigma[A(i) * \text{LinkCount}(i,k)/\text{TotalDiSacLinks}(i)] \quad (10)$$

where the sum is computed over all components; TotalDiSacLinks(i) is the number of disaccharide links found in component i; and LinkCount(i,j) is the number of the pairs of elements $\{z_r, z_{r+1}\}$ found in component i that contains the disaccharide link "-$\text{link}_j$". In other words LinkCount(i,j) is the number of pairs of elements $\{z_r, z_{r+1}\}$ containing the disaccharide link "-$\text{link}_j$-" found in S(x,y) where x=i and y can take on all possible values.

An HSGAG mixture that has undergone enzyme digestion can be represented by the function Digest(s), which contains the functions DigestS and DigestA defined as shown in Equations 11 and 12 as follows:

$$z = \text{Digest}S(x,y) \quad (11)$$

$$a = \text{Digest}A(x) \quad (12)$$

where z belongs to $\{z_1, z_2, z_3 \ldots, z_{2n}\}$; x and y are integers; x denotes the component number; y denotes the position in the component; and a is the relative abundance. After the mixture is digested by an enzyme, any of the experimental measurements that can be performed on the original undigested mixture can also be performed on the digested mixture. These measurements include, for example, mass spectroscopy and 2D NMR. If $T_e$ is the transform that represents the enzyme digest and $T_m$ is the transform that represents the mass spectroscopy measurement, then mass spectroscopy measurement performed on a mixture that has undergone enzyme digest can be represented as $T_m[T_e\{F(s)\}]$, where transformation $T_e$ represents the set of functions, Digest (s), and can be written as shown in Equation 13:

$$T_e\{F(s)\} = \text{Digest}(s) \quad (13)$$

where Digest(s) contains the functions DigestS and DigestA shown in Equations 11 and 12, and where DigestS(q,r) can be constructed from S(u,v) by performing the subroutine shown in Table 7.

TABLE 7

Subroutine for constructing DigestS(q, r) from S(u, v)

```
For all u do
    LastCut = 1
    For all v do
        If (Link {S(u,v), S(u,v+1)} = EnzymeLink)
        [where EnzymeLink is the link cut by the enzyme]
        Then
            Copy Subsequence from LastCut to v into DigestS ( )
            LastCut = v
```

DigestA(q) can then be expressed as $\Sigma[A(k)]$, the sum over all k such that the $k^{th}$ component of DigestS( ) is a sub-component of the kth component of S( ).

Step 112 of the method of FIG. 1 is the determination of whether all candidates have been considered. If not, step 106 is repeated again for another candidate solution. If so, step 114 determines whether all measurements have been considered. If all measurements have not been considered, the method continues with a different experimental measurement of the polymeric mixture. It is possible that only one measurement is necessary. However, in most embodiments, a plurality of measurements are necessary to adequately narrow the candidate solution for characterization of the polymeric mixture. Once all the measurements have been considered, the polymeric mixture is characterized in step 116 using one or more of the remaining candidate solutions.

Figure 2:
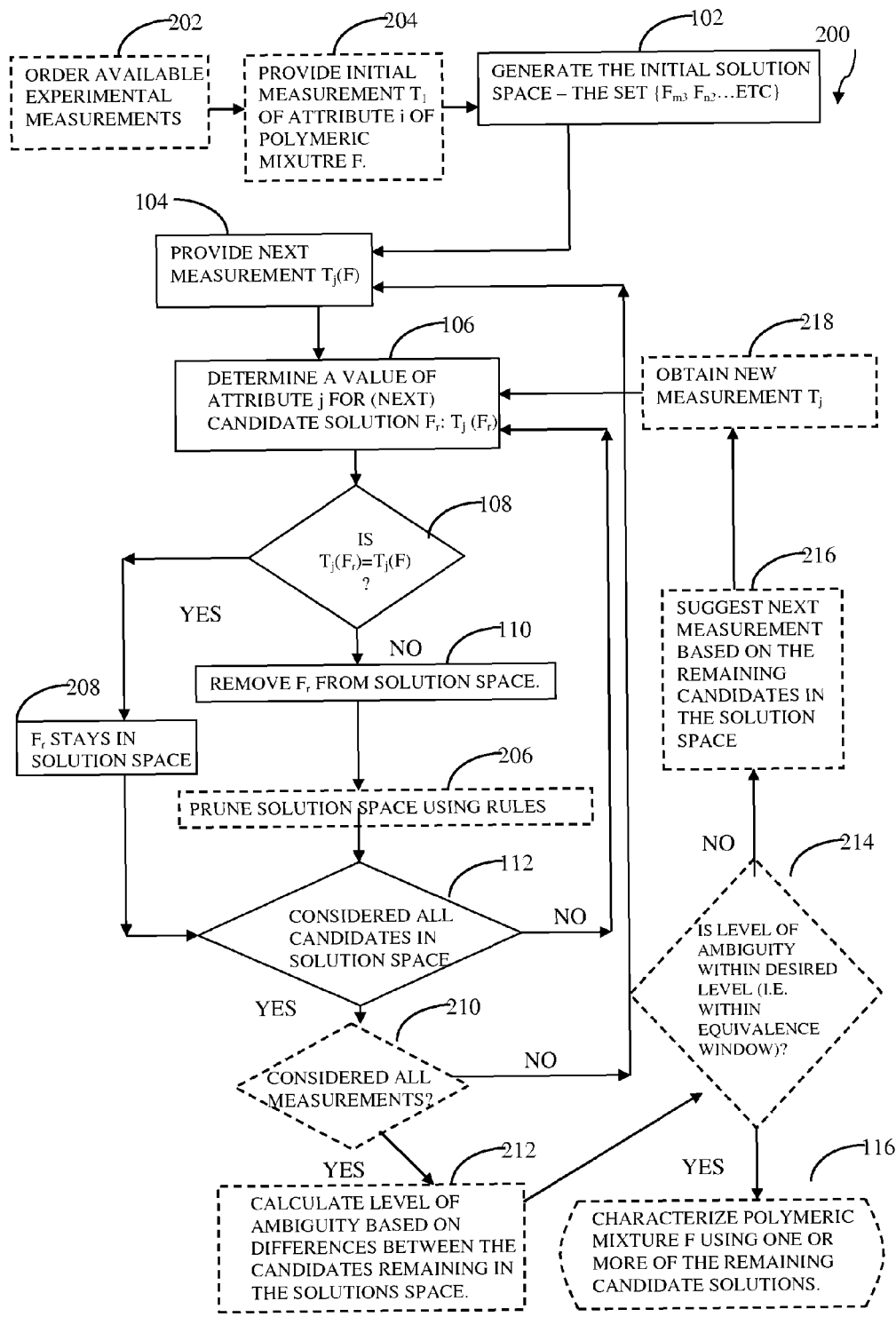
FIG. 2 is a block diagram showing steps in a method for characterizing a polymeric mixture from a set of candidate solutions, the method featuring steps for ordering measurements, pruning the solution space, and computing a measure of ambiguity among remaining candidate solutions, according to an illustrative embodiment of the invention.

FIG. 2 is a block diagram showing a solution candidate elimination procedure that includes the steps from FIG. 1, as well as additional optional steps, according to one embodiment of the invention. As in FIG. 1, dashed lines indicate optional steps in the embodiment shown.

Step 202 of FIG. 2 is the optional step of ordering the available experimental measurements of the polymeric mixture of interest in a way that will more quickly converge to an acceptably small set of one or more remaining candidate solutions. Measurements are ordered based on the kind of information the measurement provides. For example, measurements that provide information about the number of different components of a polymeric mixture, the relative abundance of each component, and the content or composition of each component are considered before measurements that provide information about how the primary units are arranged in the components. In an example in which a heparin or heparin sulfate-like glycosaminoglycans (HLGAG) mixture is being characterized, capillary electrophoresis (CE) measurements and mass spectroscopy measurements may be ordered ahead of 2D-NMR and enzymatic digest-based measurements. More specifically, an example ordering of experiments in the characterization of a HLGAG mixture may include: (i) mass spectroscopy, (ii) CE, (iii) 1D-NMR, (iv) 2D-NMR, and (v) enzymatic digest measurements.

Figure 3:
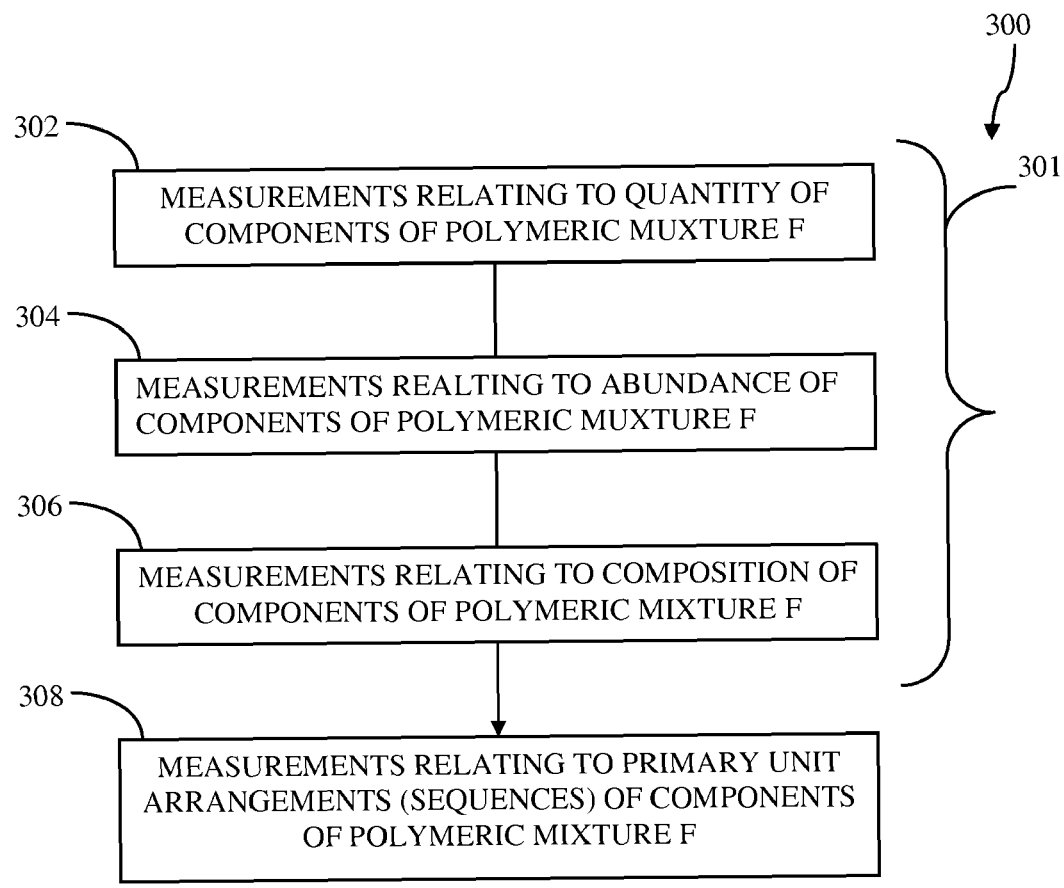
FIG. 3 is a block diagram illustrating steps for ordering available experimental measurements for use in characterizing a polymeric mixture from a set of candidate solutions, according to an illustrative embodiment of the invention.

FIG. 3 is a block diagram 300 further illustrating steps for ordering available experimental measurements, as indicated in step 202 of the method of FIG. 2 for characterizing a polymeric mixture from a set of candidate solutions. Here, bracket 301 indicates measurements relating to quantity (number) of species 302, abundance of one or more components in the mixture 304, and/or composition of one or more components in the mixture 306. These measurements 301 are preferentially used in the method of FIG. 2 to eliminate candidate solutions before measurements 308 relating to the sequence of primary units of one or more components of the mixture.

Step 204 in FIG. 2 is the step of providing an initial measurement $T_i$ of attribute i of the polymeric mixture (F) in order to generate the initial solution space of step 102. In this step, a range of candidate solutions is determined based on the initial measurement. Step 102 is described in more detail herein above.

Steps 210, 212, and 214 of FIG. 2 involve analysis of remaining candidate solutions following stepwise elimination with an initial set of measurements. A resulting measure of difference between mixtures may be used to determine a level of ambiguity, or difference, between candidates remaining in the solution space after stepwise elimination. The difference between mixtures remaining in the solution space may be determined to be within a desired range or beneath a maximum level such that all remaining mixtures are biologically equivalent.

Figure 4:
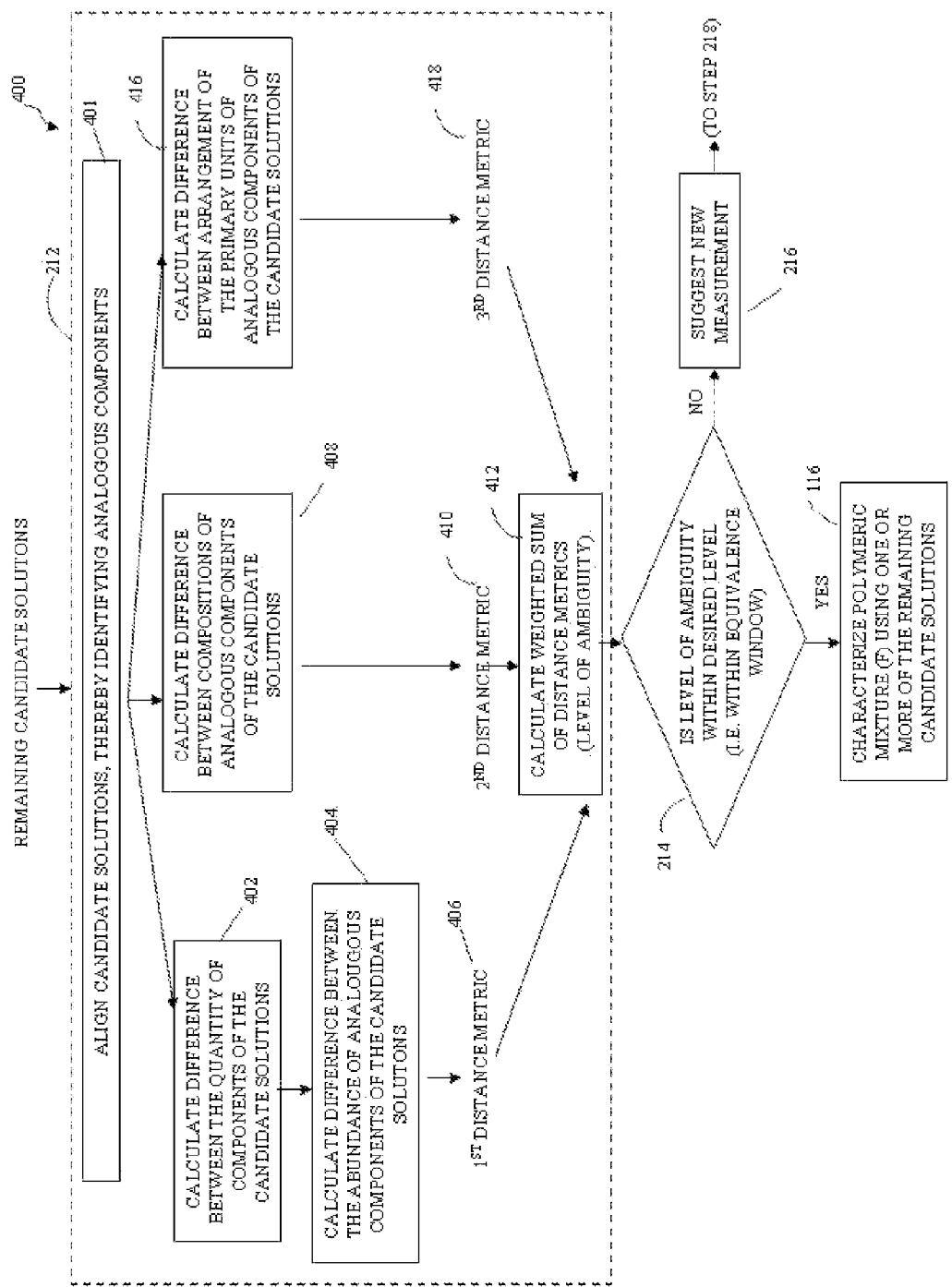
FIG. 4 is a block diagram illustrating steps for computing a measure of ambiguity among candidate solutions in a method for characterizing a polymeric mixture, according to an illustrative embodiment of the invention.

FIG. 4 is a block diagram 400 further illustrating steps for computing a measure of difference, or ambiguity, among candidate solutions, as indicated in step 212 of the method of FIG. 2. Generally, two mixtures do not have to be identical to have the same biological activity, from the perspective of therapeutics. It may be sufficient if they are similar. In the mixture characterization method of FIG. 2, step 212 involves computing a distance metric to reflect the degree of similarity (and, therefore, difference) between two mixtures. One of the problems in the manufacture of complex biologics therapeutics is that there can be batch to batch variation of a drug that must be controlled, lest there be a difference in the biological activity between batches. It is, therefore, useful to define allowable ranges, or windows, for these complex biologics. A distance metric can be used to define such windows. Methods for defining an allowable range using average molecular weight or primary unit composition are often inadequate, since mixtures that have different biological activity can have similar average molecular weight or similar primary unit composition. The allowable windows for specific complex biologics can be better defined as ranges using a multi-component and/or multi-dimensional distance metric approach.

FIG. 4 shows a detailed view of step 212 in the method of FIG. 2 for characterizing a polymeric mixture of interest, in which a distance measure is computed for two or more candidate mixtures. The overall distance metric that is computed is a weighted sum of three distance metrics. The first distance metric 406 quantifies the difference in the number of components of the compared candidate mixtures 402, as well as the difference in the abundance of the components of the compared mixtures 404. The second distance metric 410 quantifies the difference in the composition of each component of the compared candidate mixtures 408. The third distance metric 418 quantifies the difference in the order/sequence (including branching) in each component of the compared candidate mixtures 416. The weights chosen to calculate the overall distance metric are based on the specific application, or type of mixture being characterized. For example, if component length and abundance are more important to biological activity (or other property of interest) than the primary unit composition and sequence within a component, then the first metric is chosen to be more highly weighted as compared with the other two metrics. In one embodiment, the overall distance metric is expressed as a three-dimensional array or vector. This can be important in applications where all three distance metrics should be considered independently.

A first step in comparing two or more complex mixtures (for example, candidate solutions) is to align them. Step 401 of FIG. 4 involves aligning candidate solutions by ordering their components, thereby identifying analogous components among the mixtures. The alignment of step 401 orders the components of each candidate based on molecular weight. If the molecular weights of two components are identical, then the relative order of the components with the same molecular weight is based on a relative order of the first building block (primary unit) of the component. If the first building blocks are identical, the relative order of the second building block of the component is taken into account, and so on. Table 8 shows an illustrative candidate mixture with components before and after ordering.

TABLE 8

Example candidate mixture before and after
alignment according to step 401 of FIG. 4

| Component number | Before alignment | After alignment |
|---|---|---|
| 1 | DD4-7 | D9 |
| 2 | D9 | 4-59 |
| 3 | D-5D | D-5D |
| 4 | 4-59 | DD4-7 |
| 5 | 4-79D9D | 4-79D9D |

Table 9 is used herein to illustrate computation of the first, second, and third distance metrics in the method of FIG. 4. Table 9 shows components of four different candidate mixtures—Mix A, Mix B, Mix C, and Mix D. In the illustrative computations that follow, Mix A is compared to Mixes B, C, and D. Each of the mixtures contains 5 components, each of different length, having abundance (Ab.) in their respective mixtures as indicated in Table 9. The table shows the components of each mixture appropriately ordered/aligned as described herein above. Once the components of the mixture have been ordered, the mixtures are compared based on three distance metrics.

TABLE 9

Example candidate mixture before and after alignment according to step 401

| MIX A | | | MIX B | | | MIX C | | | MIX D | | |
|---|---|---|---|---|---|---|---|---|---|---|---|
| # | Sequence | Ab. | # | Sequence | Ab. | # | Sequence | Ab. | # | Sequence | Ab. |
| 1 | 4-5 | 330 | 1 | 4-5 | 310 | 1 | 4D | 330 | 1 | D9 | 330 |
| 2 | DD-5 | 450 | 2 | DD-5 | 470 | 2 | DD-5 | 450 | 2 | 4-5D | 450 |
| 3 | DDDD | 373 | 3 | DDDD | 350 | 3 | DDD-5 | 373 | 3 | D4-7D | 373 |
| 4 | 4-7DD9 | 245 | 4 | 4-7DD9 | 270 | 4 | 4-7DD9 | 245 | 4 | D-5DDD | 245 |
| 5 | D4-59DD | 156 | 5 | D4-59DD | 125 | 5 | D4-59DD | 156 | 5 | D4-59DD | 156 |

The first distance metric 406 in FIG. 4 quantifies a comparison between the number of components 402 and their abundances 404 in the different candidate mixtures. In the example of Table 9, Mix A has the same number of components as Mixes B, C, and D. Analogous components of Mixes A, B, C, and D (following alignment step 401) have identical lengths. The difference in abundances between two mixtures after component alignment can be represented as shown in Equation 14:

$$C_1 = \Sigma \text{abs}\{A_i - B_i\}/(\Sigma A_i) \tag{14}$$

where the sums are over all components (i=1 to 5); abs represents absolute value; $A_i$ represents the abundance of component i of Mix A; and $B_i$ represents the abundance of the analogous component of Mix B. Using Equation 14, the first distance metric 406 between Mix A and Mix B is computed as (330−310)+(470−450)+(373−350)+(270−245)+(156−125)/(330+450+373+245+156)=0.077. The first distance metric between Mix A and Mix C is 0, and the first distance metric between Mix A and Mix D is 0. In the case where two compared mixtures A and B do not have the same number of components, for example, where Mix A contains component i, but Mix B does not contain component i, the abundance $B_i$ is set equal to zero in Equation 14.

The second distance metric 408 quantifies a comparison of the compositions of analogous components 408 of the different candidate mixtures. The second distance metric 408 can be represented as in Equation 15:

$$C_2 = \Sigma(D_i/N_i)*R_i \tag{15}$$

where $D_i$ is the number of primary units (elements) that are different in the analogous components; $N_i$ is the number of elements in the analogous component; and $R_i$ is the relative abundance of the component in the base mixture (here, Mix A). In the example of Table 9, the second distance metric 410 between Mix A and Mix B is 0. For Mix A and Mix C, two analogous components are different. Each component differs by one element. The second distance metric 410 between Mix A and Mix C is then computed as (0.21*0.5)+(0.24*0.25)=0.165. For Mix A and Mix D, four analogous components are different. The second distance metric 410 between Mix A and Mix D is then computed as (0.21*1.0)+(0.29*0.333)+(0.24*0.5)+(0.16*0.6)=0.523.

The third distance metric 418 quantifies a comparison of the order/arrangement of primary units in analogous components of two or more candidate mixtures. The third distance metric 418 is related to the second distance metric 410. This is because if components have different primary unit composition, they will also have different order/arrangement. On the other hand, fragments having the same composition could have different order/arrangement. The third distance metric 418 can be represented as in Equation 16:

$$C_3 = \Sigma(P_i/N_i)*R_i \tag{16}$$

where $P_i$ is the number of positions that are different in the analogous components; $N_i$ is the number of elements in the analogous component; and $R_i$ is the relative abundance of the component in the base mixture (here, Mix A). In the example of Table 9, the third distance metric 418 between Mix A and Mix B is 0 because $P_i=0$ for each pair of analogous components. For Mix A and Mix C, two components are different. Each component is different in one position. The third distance metric 418 between Mix A and Mix C is then computed as (0.21*0.5)+(0.24*0.25)=0.165. For Mix A and Mix D, four components are different. The third distance metric 418 between Mix A and Mix D is then computed as (0.21*1)+ (0.29*1)+(0.24*0.5)+(0.16*0.6)=0.716.

The overall distance metric calculated in step 412 of FIG. 4 is a weighted sum of the three metrics, as indicated in Equation 17:

$$C_1*W_1+C_2*W_2+C_3*W_3 \qquad (17)$$

where $W_1$, $W_2$, and $W_3$ are weights, which can be chosen according to the particular mixture being characterized. For example, if length and abundance is more important than the composition and order within a given component, then the first metric would be highly weighted compared to the other two metrics. In the example of Table 9, using a distance metric in which length and abundance are weighted highly, Mix A is more similar to Mix D than Mix B or Mix C. Components of the overall distance metric may alternately be expressed in terms of a 3D array or vector, as shown in Equation 18:

$$C_1 i+C_2 j+C_3 k \qquad (18)$$

In one embodiment, the overall distance metric is used to identify bio-equivalent mixtures, for example, in the manufacture of bio-equivalent versions of therapeutics. For example, the method of FIG. 2 may be used to identify a biopolymer mixture of interest having either a known or unknown composition. Experimental measurements are performed on the biopolymer mixture, and the elimination procedure of FIG. 2 results in the identification of multiple candidate solutions whose transformation values satisfy Equation 3, indicating that each of the candidate solution mixtures would produce the same measured values (within acceptable tolerance) as the mixture of interest. An overall distance metric may be computed as described herein above to quantify the "difference" between each remaining candidate solution and the mixture of interest. Each candidate whose distance metric is below an acceptable level is considered "bio-equivalent" and can be used instead of the mixture of interest in therapeutic applications. In another embodiment, the overall distance metric is used to identify bio-equivalent mixtures without application of the candidate elimination procedure of FIG. 2.

In addition to determination of an overall distance metric, other optional steps to optimize performance of the mixture characterization method shown in FIG. 2 include pruning the solution space (step 206) based on rejected candidate solutions, and suggesting additional measurements (step 216) based on a summary of the remaining solution space.

Step 206 of the characterization method of FIG. 2 involves pruning of the solution space after a candidate solution has been eliminated. Pruning of the solution space refers to the process in which candidates are removed from the solution space without explicitly evaluating a value of an attribute to determine if it is a valid member of the solution space. Indexing and storing the candidate solutions in a "tree" aids the pruning process, as well as the initial generation of the candidate solutions in step 102 of FIG. 1. This is particularly important where the number of candidate solutions in the solution space is very large (for example, $10^{10}$ or more candidate solutions). With regard to pruning, the indexing and storing of candidate solutions in the manner described herein enables the removal of all candidates in a group or sub-group when one element in the group or sub-group does not acceptably match the value of the measured attribute, as determined in step 108 of FIG. 1. For example, if one candidate solution belonging to a related set of candidate solutions is removed because it does not match a given measured attribute of the mixture of interest, then all the other elements in the set of related candidates can be removed without explicitly evaluating each of the candidates in the set, as long as the relationship of the candidates has to do with the measured attribute. Furthermore, grouping and indexing the candidate solutions allows generation of the initial solution space without identifying every specific candidate solution. For example, it may be sufficient to identify one or more levels of groupings before "filling out" each sub-grouping with specific candidate solutions. This feature is described in more detail in the discussion of FIG. 5, for example.

Figure 5:
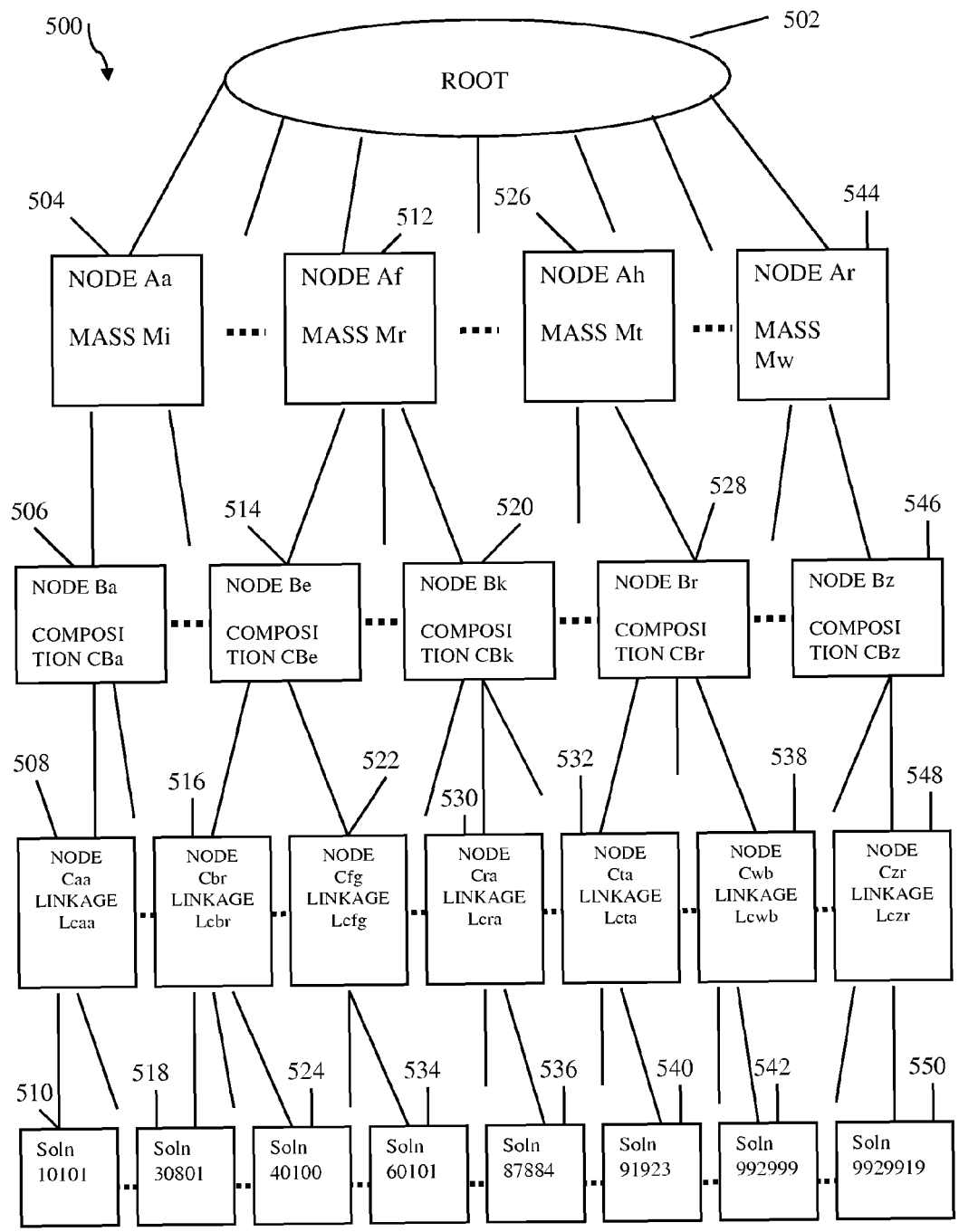
FIG. 5 is a block diagram illustrating a candidate solution tree for indexing and storing candidate solutions during the generation and/or pruning of candidates in a method for characterizing a polymeric mixture, according to an illustrative embodiment of the invention.

FIG. 5 is a schematic 500 illustrating a candidate solution tree for indexing and storing candidate solutions during the generation of candidates (for example, step 102 of the method of FIG. 1) and/or during the pruning of candidates (for example, step 206 of the method of FIG. 2). The root 502 is the basis upon which all branches of the tree and all candidate solutions (the leaves of the tree) are characterized. The tree is organized by nodes, which indicate where a given branch divides into sub-branches. Each node is labeled. All of the candidate solutions that can be traced from a given node satisfy the condition represented by the label.

In the illustrative example shown in FIG. 5, the tree has three levels of nodes that organize the candidate solutions into various groups and sub-groups. The first level includes nodes 504, 512, 526, and 544, and organizes the candidate solutions in terms of their mass. The second level includes nodes 506, 514, 520, 528, and 546, and organizes the candidate solutions in terms of their primary unit composition. The third level includes nodes 508, 516, 522, 530, 532, 538, and 548, and organizes the candidate solutions in terms of the linkage, or arrangement, of primary units in the components of the mixture represented by the candidate solution. The candidate solutions represented in FIG. 5 include 510, 518, 524, 534, 536, 540, 542, and 550. Other embodiments may contain a greater or lesser number of node levels, according to the application.

In the example shown in FIG. 5, candidate solutions 30801 to 40100 contain the same linkage information represented by the label Linkage LCbr. They are descendants of the Node Cbr. Candidate Solutions 30801 to 60101 contain the same combination information represented by the label Composition CBe. They are descendants of the Node Be. Candidate Solutions 30801 to 87881 contain the same mass information represented by the label Mr. They are descendants of the Node Af.

In one example, a related set of candidate solutions represent mixtures that each have the same number of primary units, identical relative abundances and identical primary unit compositions for each of its components, but a different order in which the primary units are arranged in at least one of its components. In another example, a related set of candidate solutions represent mixtures that each have identical relative amounts of primary units in the overall mixture. When applying transformations related to compositional analysis, where an element of the solution space does not have the same composition as the mixture of interest, the set of these related candidates in the solution space with the same composition can also be eliminated without explicitly evaluating a transform for each candidate.

Pruning the solution space may also involve appropriate arrangement of the elements of the solution space based on the properties of the specific class of mixtures of interest and the analytical measurements available. For example, in the case of HSGAG mixtures, the primary units that make up the components of the mixture are a known set of all possible disaccharide units. However, the relative abundances of the monosaccharide composition can be determined by obtaining 1D NMR measurements. This is in addition to a compositional analysis to determine relative abundances of the disaccharide units. Thus, the elements in the solution space can be organized based on the monosaccharide composition, and related elements can be pruned from the solution space as described above.

Table 10 represents a subset of candidates in a solution space. The candidates S1, S2, and S3, have analogous components with identical relative abundances, where the components differ only in their arrangement of primary units. In an illustrative application of the characterization method of FIG. 2, it is determined that the solution represented by S1 does not satisfy the transform modeling the capillary electrophoresis (CE) measurement, as described herein above. Therefore, solutions S2 and S3 also will not satisfy the condition in step 108, and these can be eliminated without determining CE values for them. This is because of the rule that candidate solutions which differ only in the arrangement of the primary units that make up their components will have the same CE value. It is, therefore, not necessary to explicitly compute the transform in step 106 to determine CE values for the candidates that are so-related, and these candidates may be eliminated. By indexing candidate solutions according to this rule, it is possible to eliminate entire branches automatically, without explicitly computing transforms for all candidates within those branches.

Step 210 of FIG. 2 is the determination of whether all measurements have been considered. If not, the next measurement is provided in step 104, and the method proceeds to step 106. In certain embodiments, further steps are performed in order to determine the next measurement that should be used in the series of candidate eliminations (for example, step 216, FIG. 2). Step 216 may be performed in addition to the initial ordering of available experimental measurements, as in step 202, or it may be performed instead of step 202. In one embodiment, step 216 involves determining the next measurement based on information about the remaining candidates in the solution space, for example, an identification of what parts of the mixture characterization cannot yet be determined (information about lack of convergence of the solution space), and/or determination of a measure of difference/ambiguity between the remaining solutions (described herein with respect to step 212).

Table 11 illustrates identification of what parts of a mixture characterization remains to be determined (lack of convergence), based on remaining candidate solutions. In the example of Table 11, the solution space contains candidate solutions S1, S2, and S3 after all transformations have been applied and all non-conforming candidates eliminated. Component number 2 is identical in all three candidate solutions. The exact position of primary unit "R" has not been determined in component 3. Also, the exact arrangement of component 1 has not been determined.

TABLE 11

Example set of candidate solutions following series of candidate eliminations

| S1 Sequence | Rel. Abund. | S2 Sequence | Rel. Abund. | S3 Sequence | Rel. Abund. |
| --- | --- | --- | --- | --- | --- |
| 1 NM | 40 | 1 MN | 40 | 1 MN | 40 |
| 2 DDN | 41 | 2 DDN | 41 | 2 DDN | 41 |
| 3 DDR | 19 | 3 DRD | 19 | 3 DDR | 19 |

Table 12 illustrates another example of the identification of lack of convergence, based on remaining candidate solutions. In this example, the exact position of primary unit "C" in component 5 has not been determined, and components 1 and 2 are different by one primary unit.

TABLE 10

Example subset of candidate solutions for illustrating example of pruning (step 206, FIG. 2)

| S1 Sequence | Rel. Abund. | S2 Sequence | Rel. Abund. | S3 Sequence | Rel. Abund. | S4 Sequence | Rel. Abund. |
| --- | --- | --- | --- | --- | --- | --- | --- |
| 1 MN | 40 | 1 MN | 40 | 1 MN | 40 | 1 MN | 40 |
| 2 DND | 33 | 2 DDN | 33 | 2 DDN | 33 | 2 NDD | 41 |
| 3 DDR | 27 | 3 DDR | 27 | 3 DRD | 27 | 3 DRD | 19 |

TABLE 12

Example set of candidate solutions following series of candidate eliminations

| | S1 Sequence | Rel. Abund. | | S2 Sequence | Rel. Abund. | | S3 Sequence | Rel. Abund. |
|---|---|---|---|---|---|---|---|---|
| 1 | AQ | 23.0 | 1 | AQ | 23.0 | 1 | AD | 23.0 |
| 2 | DDQ | 23.0 | 2 | DDQ | 23.0 | 2 | DQQ | 23.0 |
| 3 | DDDD | 26.0 | 3 | DDDD | 26.0 | 3 | DDDD | 26.0 |
| 4 | AKDDC | 17.0 | 4 | AKDDC | 18.8 | 4 | AKDDC | 17.1 |
| 5 | DAQDDC | 10.9 | 5 | DAQCDD | 9.2 | 5 | DAQDCD | 10.9 |

Depending on what the differences are between the remaining candidates, further analytical methods can be suggested to distinguish the candidates. Thus, step 216 in the mixture characterization method of FIG. 2 involves using the identification of lack of convergence following one or more elimination sequences, and/or using a distance metric (equivalence window) computed in step 212 to suggest additional measurements for use in further narrowing the candidate solution space.

The invention may be more fully understood by reference to the following non-limiting examples.

EXAMPLE 1

Characterization of an HSGAG Mixture

In one embodiment, characterization of an HSGAG mixture involves the use of Matrix Assisted Laser Desorption/Ionization Mass Spectroscopy (MALDI-MS) measurements, as well as NMR spectroscopy measurements. For example, for MALDI-MS, analyses can be carried out on a PerSeptive Biosystems Voyager Elite reflectron time-of-flight instrument in the linear mode with delayed extraction. The oligosaccharide spot can be prepared by adding 1 μL of matrix solution (12 mg/mL caffeic acid in 30%-70% acetonitrile) that contains 0.5-5 μM basic peptide $(RG)_{15}$ (calculated mass of the $(M+H)^+$ ion=3217.6), and by allowing the spot to crystallize. The instrument settings can be 22 kV, grid at 93%, guide wire at 0.15%, pulse delay 150 ns, and low mass gate at 1,000, 128 shots averaged. The $(M+H)^+$ ions of the basic peptide and the $(M+H)^+$ ion of a 1:1 peptide:saccharide complex are observed in each mass spectrum. The mass of the saccharide can be determined by subtracting the measured m/z value of the $(M+H)^+$ ion of the peptide from that of the 1:1 complex. To ensure accurate mass measurement, all spectra on a plate can be calibrated externally using a standard of $(RG)_{19}R$ and its complex with a nitrous acid-derived hexasaccharide, $I_{2S}H_{NS,6S}I_{2S}H_{NS,6S}I_{2S}Man_{6S}$ (calculated mass of 1655.4), under identical instrument parameters.

For NMR spectroscopy, one-dimensional (1-D) and two-dimensional (2-D) NMR spectra can be obtained using a 500 MHz Bruker Avance spectrometer equipped with a 5 mm TXlz probe, and/or a 600 MHz Bruker Avance spectrometer equipped with a 5 mm TClz cryoprobe. The 600 MHz spectrometer with the TClz probe provides enhanced sensitivity. Samples can be dissolved in $^2H_2O$ (99.9%) and freeze dried to remove residual water. After exchanging the samples twice, they can be dissolved in 0.6 ml of $^2H_2O$ (99.99%). Chemical shifts are given in ppm downfield from sodium trimethylsilyl propionate as external standard (precision of +0.003 ppm). The experiments can be conducted between 20° C. to 70° C. Carbon NMR spectra are obtained using 400 MHz Bruker AMX spectrometer equipped with a 10 mm probe. Proton NMR spectra are recorded with presaturation of residual water signal, with a recycle delay of 12 s. 2D homonuclear correlation spectra (DQF-COSY, TOCSY and NOESY/ROESY) can be acquired in the phase sensitive mode using TPPI and Fourier transformed into a data matrix of 4×2K with a phase shifted (π/3) square sine bell function. The $^1H/^{13}C$ chemical shift correlation (HSQC) spectra can be obtained using z gradients for coherence selection. These are obtained with carbon decoupling during acquisition period in phase sensitivity-enhanced pure absorption mode. The spectra are acquired with a nulling time of 2S, 1024 data points in F2, 512 increments in F1. The final matrix size is zero-filled to 4K×2K and multiplied with shifted (π/3) sine-bell-square prior to Fourier transformation.

Figure 6:
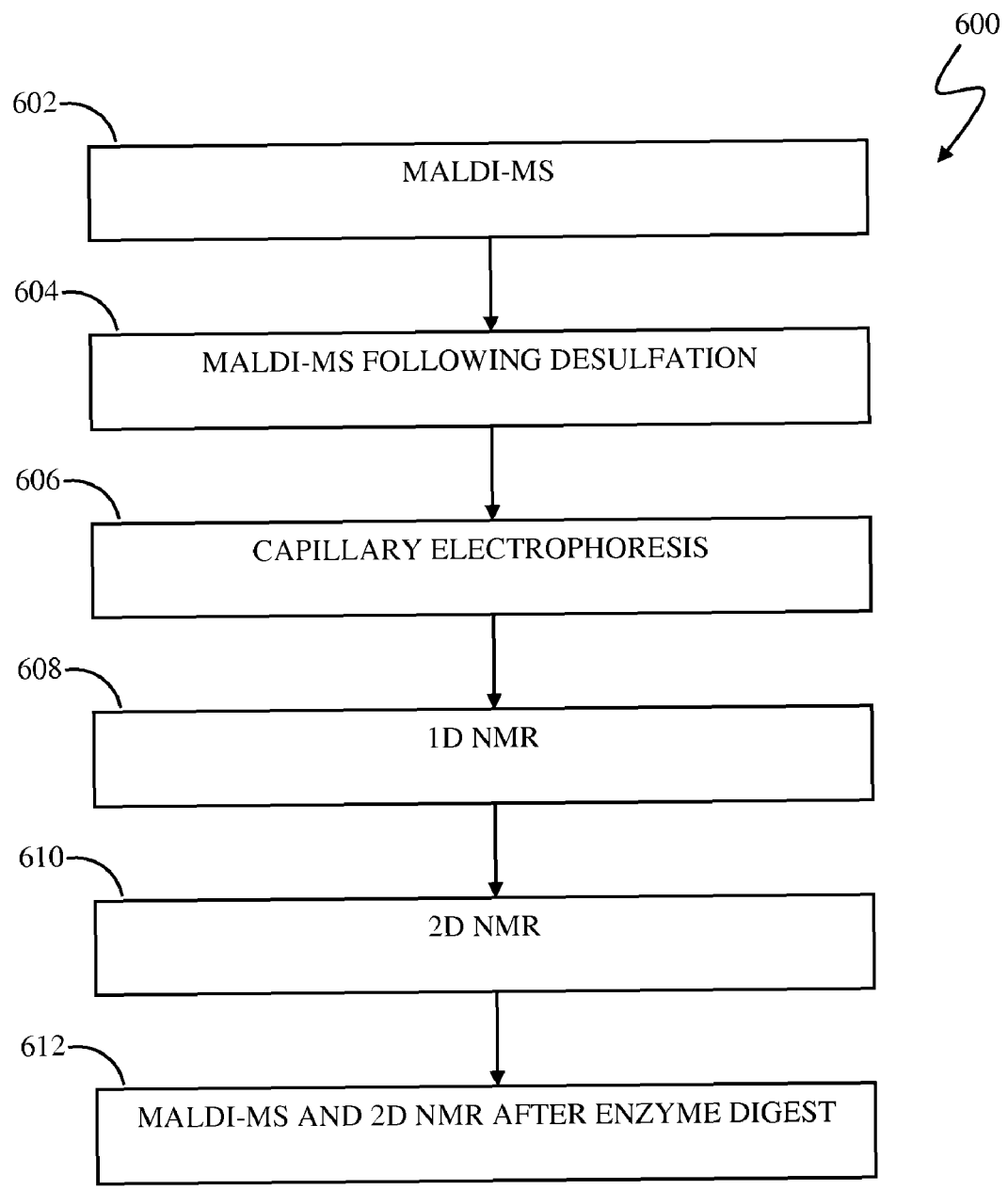
FIG. 6 is a block diagram illustrating an exemplary ordering of experimental measurements in the characterization of a glycan mixture, according to an illustrative embodiment of the invention.

FIG. 6 is a block diagram 600 illustrating an exemplary ordering of experimental measurements in the characterization of a glycan mixture, for example, an HSGAG mixture, according to the candidate elimination procedure of FIG. 2. Matrix Assisted Laser Desorption/Ionization Mass Spectroscopy (MALDI-MS) measurement 602 of the mixture to be characterized is used to generate the initial candidate solution space (step 102 in the method of FIG. 1 or FIG. 2). An exemplary MALDI-MS measurement is shown in Table 13. Although the peak information is useful, the relative peak height cannot be accurately used to determine relative amounts. The total number of candidate solutions in the initial solution space is very large—on the order of about $10^{25}$ candidates.

TABLE 13

Exemplary MALDI-MS measurement

| Mass | Peak height |
|---|---|
| 2209.82 | 140 |
| 2129.76 | 200 |
| 2247.84 | 370 |
| 2327.9 | 475 |
| 2049.70 | 213 |

The HSGAG candidate elimination method proceeds using a MALDI mass spectroscopy measurement of the mixture of interest following desulfation (reference 604, FIG. 6). The quantitative information provided by peak height is accurate. An exemplary MALDI-MS measurement following desulfation is shown in Table 14. After elimination of candidate solutions in the method of FIG. 2 based on this measurement, there are on the order of about $10^{20}$ candidate solutions remaining.

TABLE 14

Exemplary MALDI-MS measurement following desulfation

| Element | Relative Abundance (%) |
|---|---|
| I or G-HNS,6S | 10.36 |
| I or G-HNAc,6S | 10.86 |
| I2S or G2S-HNS,6S | 63.62 |
| I2S or G2S-HNS | 8.61 |
| I or G-HNS,3S,6S | 6.55 |

The HSGAG candidate elimination method proceeds using a capillary electrophoresis measurement of the mixture of interest (reference 606, FIG. 6). After elimination of candidate solutions in the method of FIG. 2 based on this measurement, there are on the order of about $10^{11}$ candidate solutions remaining. For example, a Hewlett-Packard 3D capillary electrophoresis unit can be used with uncoated fused silica capillaries (i.d. 75 mm, o.d. 363 mm, $I_{det}$ 72.1 cm, and $I_{tot}$ 80.5 cm). In one embodiment, analytes are monitored using UV detection at 230 nm (20) and an extended light path cell (Hewlett-Packard). The electrolyte is a solution of 10 mM dextran sulfate and 50 mM trisyphosphoric acid (pH 2.5). Dextran sulfate is used to suppress nonspecific interactions of HLGAG oligosaccharides with the silica wall. Separations are carried out at 30 kV with the anode at the detector side (reversed polarity). A mixture of 1,5-naphthalenedisulfonic acid and 2-naphthalenesulfonic acid (10 mM each) is used as internal standard where indicated. Alternatively, other experimental protocols may be followed.

The HSGAG candidate elimination method proceeds using a 1-D NMR measurement (reference 608, FIG. 6). This measurement provides information about the monosaccharide composition of the mixture. An exemplary 1D-NMR measurement is shown in Table 15. After elimination of candidate solutions in the method of FIG. 2 based on this measurement, there are about $1.5 \times 10^6$ candidate solutions remaining.

TABLE 15

Exemplary 1-D NMR measurement

| Element | Relative Abundance (%) |
|---|---|
| I | 5.43 |
| G | 8.46 |
| I2S | 36.11 |
| HNS | 4.31 |
| HNAc,6S | 5.43 |
| HNS,6S | 36.99 |
| HNS,3S,6S | 3.28 |

The HSGAG candidate elimination method proceeds using a 2-D NMR measurement (reference 610, FIG. 6). This measurement provides information about linkages between disaccharide building blocks (primary units). An exemplary 2D-NMR measurement is shown in Table 16. After elimination of candidate solutions in the method of FIG. 2 based on this measurement, there are 15 candidate solutions remaining.

TABLE 16

Exemplary 2-D NMR measurement

| Left Element | Right Element | Relative Amount (%) |
|---|---|---|
| HNAc,6SS | G | 14.48 |
| HNS,6S | G | 8.07 |
| HNS,3S,6S | I2S | 8.74 |
| HNS,6S | I2S | 57.23 |
| HNS | I2S | 11.49 |

The HSGAG candidate elimination method proceeds using MALDI-MS and 2-D NMR measurements following enzyme digest by Heparinase 1 (reference 612, FIG. 6). Exemplary measurements are shown in Table 17 and Table 18. After elimination of candidate solutions in the method of FIG. 2 based on these measurements, there is one candidate solution remaining. Table 19 shows the complete characterization of the HSGAG mixture of interest. Thus, the HSGAG mixture is characterized by this candidate solution (step 116, FIG. 2).

TABLE 17

Exemplary MALDI-MS measurement following Hep 1 digestion

| Mass | Peak Height |
|---|---|
| 577.47 | 2642 |
| 595.49 | 432 |
| 1054.88 | 350 |
| 974.81 | 230 |
| 1092.9 | 323 |
| 497.41 | 460 |

TABLE 18

Exemplary 2-D NMR measurement following Hep 1 digestion

| Left Element | Right Element | Relative Abundance (%) |
|---|---|---|
| HNAc,6S | G | 64.24 |
| HNS,6S | G | 35.76 |

TABLE 19

Exemplary complete characterization of HSGAG mixture of interest

| # | Formula | Length | Mass | Rel. Abund. (%) |
|---|---|---|---|---|
| 1 | I-HNAc,6S G-HNS,3S,6S I2S-HNS,6S I2S-HNS,6S | 4 | 2209.82 | 9.0 |
| 2 | I-HNAc,6S G-HNS,3S,6S I2S-HNS I2S-HNS,6S | 4 | 2129.76 | 17.2 |
| 3 | I2S-HNS,6S G-HNS,6S I2S-HNS,6S I2S-HNS,6S | 4 | 2247.84 | 24.2 |
| 4 | I2S-HNS,6S I2S-HNS,6S I2S-HNS,6S I2S-HNS,6S | 4 | 2327.9 | 32.4 |
| 5 | I-HNAc,6S G-HNS,6S I2S-HNS I2S-HNS,6S | 4 | 2049.7 | 17.2 |

EXAMPLE 2

Characterization of a Glycoprotein Mixture

In addition to HSGAG mixtures, glycoprotein mixtures can also be characterized using the method of FIG. 2. Each unique component in a glycoprotein mixture includes a peptide backbone with various branched polysaccharides linked to the peptide backbone. The branched polysaccharides are referred to as glycoforms and the places where the glycoforms are linked to the peptide backbone are called glycosylation sites.

Tables 20, 21, and 22 depict a characterization of an illustrative glycoprotein mixture of interest, which may be determined using the method of FIG. 2. Table 20 characterizes the components of the mixture, each having a peptide backbone and attached glycoforms; Table 20 also shows the locations where the glycoforms are attached to the backbone. Table 21 characterizes the sequence of the peptide backbones present in the mixture. Table 22 characterizes the sequence of the branched glycoforms in the mixture.

TABLE 20

Example characterization of components of glycoprotein mixture of interest

| Component Number | Sequence | Relative Abundance (%) |
|---|---|---|
| 1 | P1(G1, 0)(G2, 14) | 25.9 |
| 2 | P2(G3, 6) | 40.6 |
| 3 | P1(G5, 14)(G4, 0) | 33.5 |

TABLE 21

Peptide backbone sequences in glycoprotein mixture of Table 20

| Peptide | Sequence | |
|---|---|---|
| P1 | NITTGCAEHCSLNENITVPD | (SEQ ID. No. 1) |
| P2 | GQALLVNSSQPWEPLQLHVDK | (SEQ ID. No. 2) |

TABLE 22

Glycoform sequences in glycoprotein mixture of Table 20

| Glycoform | Sequence |
|---|---|
| G1 | Galb4GlcNAcb2Mana3(GlcNAcb2Mana6)(GlcNAcb4)Manb4GlcNAcb4(Fuca6)GlcNAc |
| G2 | Fuca3(Galb4)GlcNAcb2Mana3(Mana6)Manb4GlcNAcb4(Fuca6)GlcNAc |
| G3 | Galb4GlcNAcb2Mana3(GlcNAcb2Mana6)Manb4GlcNAcb4(Fuca6)GlcNAc |
| G4 | GlcNAcb2Mana3(Mana6)Manb4GlcNAcb4(Fuca6)GlcNAc |
| G5 | Galb4GlcNAcb2Mana3(Mana6)Manb4GlcNAcb4(Fuca6)GlcNAc |

Experimental measurements and rules that can be integrated in the method of FIG. 2 to characterize a glycoprotein mixture include, for example, mass spectroscopy measurements such as MALDI-MS and/or electrospray-mass spectroscopy (ES-MS), monosaccharide composition measurements, amino acid composition measurements, peptide sequence measurements, carbohydrate protein binding measurements, measurements following enzymatic digest of peptides and/or glycoprotein, and biosynthetic rules of assembly for branched polysaccharides. In addition, information from databases of existing glycoforms can be used to prune glycoform candidates from the solution space (for example, step 206 of the method of FIG. 2). Amino acid composition and peptide sequencing rules are described, for example, in Berg, Tymoczko, and Stryer (2002) Biochemistry, W.H. Freeman & Co.

Figure 7:
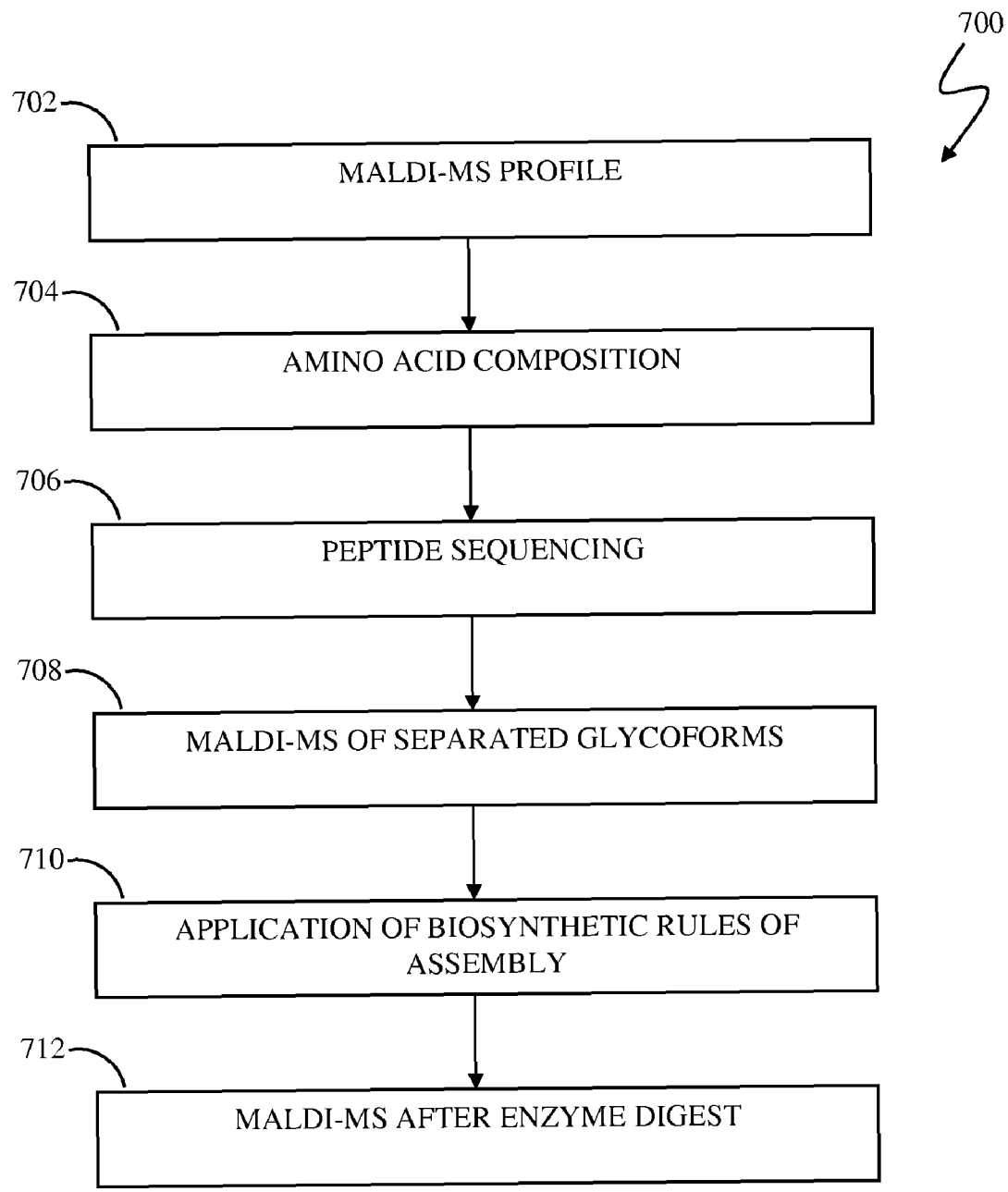
FIG. 7 is a block diagram illustrating an exemplary ordering of experimental measurements in the characterization of a glycoprotein mixture, according to an illustrative embodiment of the invention.

FIG. 7 is a block diagram 700 illustrating an exemplary ordering of experimental measurements in the characterization of a glycoprotein mixture, according to the candidate elimination procedure of FIG. 2. A MALDI-MS profile 702 of the glycoprotein mixture to be characterized is used to generate the initial candidate solution space (step 102 in the method of FIG. 1 or FIG. 2). An exemplary MALDI-MS profile is shown in Table 23. The total number of candidate solutions in the initial solution space is very large—on the order of about $10^{20}$ candidates.

Example experimental protocols for performing MALDI-MS of glycoproteins are described in the following publications: (1) Andersen et al. (1996), "Electrospray ionization and matrix assisted laser desorption/ionization mass spectrometry: powerful analytical tools in recombinant protein analysis," *Nat Biotechnol,* 14, 449-57; and (2) Dalluge (2002), "Mass spectrometry: an emerging alternative to traditional methods for measurement of diagnostic proteins, peptides and amino acids," *Curr Protein Pept Sci,* 3, 181-90.

In one embodiment in which MALDI-MS of glycoproteins is performed, N-glycans are released by peptide:N-glycanase (PNGase F) treatment. MALDI data can be acquired, for example, using a Perspective Biosystems Voyager-DE STR mass spectrometer in the reflectron mode with delayed extraction. The extracted samples are dissolved in 10 µL of methanol, and 1 µL of dissolved sample is premixed with 1 µL of a matrix—for example, 2,5-dihydrobenzoic acid—before loading onto a 100-well stainless steel sample plate. Alternative experimental protocols may be used.

TABLE 23

Exemplary MALDI-MS profile in the characterization of a glycoprotein mixture of interest

| Molecular Weight | Peak Intensity |
|---|---|
| 5510.04 | 29.7 |
| 3966.96 | 37.8 |
| 4795.44 | 38.13 |

The glycoprotein candidate elimination method proceeds using a measurement of amino acid composition (reference 704, FIG. 7). In a portion of the sample to be tested, the protein is separated from the carbohydrate, and the amino acid composition is determined. An exemplary amino acid composition determination is shown in Table 24. After elimination of candidate solutions in the method of FIG. 2 based on this measurement, there are on the order of about $10^{10}$ candidate solutions remaining.

TABLE 24

Exemplary amino acid composition, used in the characterization of a glycoprotein mixture

| Amino Acid | % Composition |
| --- | --- |
| D (aspartic acid) | 4.9 |
| C (cycteine) | 5.88 |
| A (alanine) | 4.9 |
| W (tryptophan) | 1.96 |
| V (valine) | 6.86 |
| T (threonine) | 8.82 |
| S (serine) | 6.86 |
| Q (glutamine) | 5.88 |
| P (proline) | 6.86 |
| N (asparagine) | 10.78 |
| L (leucine) | 10.78 |
| K (lysine) | 1.96 |
| I (isoleucine) | 5.88 |
| H (histidine) | 4.90 |
| G (glycine) | 4.90 |
| E (glutamic acid) | 7.84 |

The glycoprotein candidate elimination method proceeds using peptide sequence measurements (reference 706, FIG. 7). This measurement provides information about the number of protein backbones in the glycoprotein mixture, as well as the sequence of the peptide backbones. Table 21 shows the sequences of the two peptide backbones in an illustrative glycoprotein mixture. After elimination of candidate solutions in the method of FIG. 2 based on this measurement, there are on the order of about $10^7$ candidate solutions remaining.

The glycoprotein candidate elimination method proceeds using MALDI-MS measurements of glycoforms separated from the glycoprotein mixture (reference 708, FIG. 7). An exemplary MALDI-MS measurement of separated glycoforms is shown in Table 25. After elimination of candidate solutions in the method of FIG. 2 based on this measurement, there are on the order of about $3 \times 10^5$ candidate solutions remaining in the solution space. Exemplary experimental protocols for performing MALDI-MS measurements of glycoforms are described in the following publications: (1) Rudd and Dwek (1997), "Rapid, sensitive sequencing of oligosaccharides from glycoproteins," *Curr Opin Biotechnol*, 8, 488-97; (2) Harvey (1999), "Matrix-assisted laser desorption ionization mass spectrometry of carbohydrates," *Mass Spectrum Rev*, 18, 349-450; and Dell and Morris (2001), "Glycoprotein structure determination by mass spectrometry," *Science*, 291, 2351-6.

TABLE 25

Exemplary MALDI-MS measurement of separated glycoforms

| Molecular Weight | Peak Intensity |
| --- | --- |
| 1828.51 | 25 |
| 1568.21 | 25 |

TABLE 25-continued

Exemplary MALDI-MS measurement of separated glycoforms

| Molecular Weight | Peak Intensity |
| --- | --- |
| 1625.31 | 40 |
| 1260.01 | 35 |
| 1422.11 | 35 |

The glycoprotein candidate elimination method proceeds by applying biosynthetic rules of assembly for branched polysaccharides (reference 710, FIG. 7). This may be supplemented by using a database of possible allowed branched polysaccharide structures. For example, a specific assembly of mannose and N-acetyl glucosamine is known to exist in all human N-linked polysaccharides. A candidate solution can be examined to see if it includes this specific assembly, where the glycoprotein mixture of interest is known to contain human N-linked polysaccharides. If the candidate solution does not include the specific assembly, it is eliminated. After elimination of candidate solutions in the method of FIG. 2 based on application of biosynthetic rules, there are 261 remaining candidate solutions in the solution space.

The glycoprotein candidate elimination method then proceeds using a MALDI-MS measurement of the mixture of interest following digestion with protease enzymes (reference 712, FIG. 7). An exemplary MALDI-MS measurement following enzymatic digestion is shown in Table 26. Peptide enzymatic digest may be performed, for example, using the EXPASy peptide cutter as described at http://us.expasy.org/tools/peptidecutter/peptidecutter_enzymes.html. After elimination of candidate solutions in the method of FIG. 2 based on MALDI-MS measurement following enzymatic digestion, there is one remaining candidate solution. Thus, the glycoprotein mixture is characterized by this candidate solution (step 116, FIG. 2). Tables 20, 21, and 22 above depict this characterization.

TABLE 26

Exemplary MALDI-MS measurement after enzyme digestion

| Molecular Weight | Peak Intensity |
| --- | --- |
| 2618.38 | 25 |
| 683.74 | 60 |
| 2207.92 | 25 |
| 3035.86 | 40 |
| 931.10 | 40 |
| 2049.88 | 35 |
| 2061.82 | 35 |

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of characterizing a heparin-like glycosaminoglycan mixture of interest, the method comprising the steps of: (a) generating a solution space comprising a plurality of candidate solutions; (b) providing an experimental measurement of a first attribute of a heparin-like glycosaminoglycan mixture of interest; (c) determining for each of at least a subset of the candidate solutions a value of the first attribute; and (d) characterizing the heparin-like glycosaminoglycan mixture of interest at least in part by eliminating at least one of the candidate solutions from the solution space whose determined value does not correspond to the experimental measurement of the first attribute.

2. The method of claim 1, wherein each of the plurality of candidate solutions is characterized by a quantity of components, and wherein each component is characterized by (i) an abundance of the component in the candidate solution, (ii) a composition defined by one or more members of a set of primary units, and (iii) an arrangement of the one or more primary units in the component.

3. The method of claim 2, wherein the abundance in element (i) is a relative abundance.

4. The method of claim 1, wherein step (d) comprises eliminating candidate solutions from the solution space in a step-wise manner according to a comparison between an experimental measurement of each of a plurality of attributes of the heparin-like glycosaminoglycan mixture of interest and a value of the respective attribute determined for each of at least a subset of the remaining candidate solutions in the solution space.

5. The method of claim 1, wherein in step (c), determining a value of the first attribute for a candidate solution comprises evaluating a model that predicts the first attribute for a mixture characterized by the candidate solution.

6. The method of claim 1, wherein in step (c), determining a value of the first attribute for a candidate solution comprises obtaining a value of the first attribute from a database.

7. The method of claim 1, wherein the experimental measurement comprises at least one member selected from the group consisting of a physical measurement, a chemical measurement, and a biological assay.

8. A method of characterizing a heparin-like glycosaminoglycan mixture of interest, the method comprising the steps of: (a) generating a solution space comprising a plurality of candidate solutions, wherein each candidate solution is characterized by a quantity of components, and wherein each component is characterized by (i) an abundance of the component in the candidate solution, (ii) a composition defined by one or more members of a set of primary units, and (iii) an arrangement of the one or more primary units in the component; (b) providing an experimental measurement of a first attribute of a heparin-like glycosaminoglycan mixture of interest; (c) determining for each of at least a subset of the candidate solutions a value of the first attribute; and (d) characterizing the heparin-like glycosaminoglycan mixture of interest at least in part by eliminating at least one of the candidate solutions from the solution space whose determined value does not correspond to the experimental measurement of the first attribute.

9. The method of claim 8, further comprising the steps of: (e) providing an experimental measurement of a second attribute of the heparin-like glycosaminoglycan mixture of interest; (f) determining for each of at least a subset of the candidate solutions a value of the second attribute; and (g)

characterizing the heparin-like glycosaminoglycan mixture of interest at least in part by eliminating at least one of the candidate solutions from the solution space whose determined value does not correspond to the experimental measurement of the second attribute.

10. The method of claim 8, wherein step (d) comprises eliminating candidate solutions from the solution space in a step-wise manner according to a comparison between an experimental measurement of each of a plurality of attributes of the heparin-like glycosaminoglycan mixture of interest and a value of the respective attribute determined for each of at least a subset of the remaining candidate solutions in the solution space.

11. The method of claim 10, wherein step (d) proceeds by preferentially eliminating candidate solutions having different quantities of components than the heparin-like glycosaminoglycan mixture of interest before eliminating candidate solutions having the same quantities of components as the heparin-like glycosaminoglycan mixture of interest but having different component compositions.

12. The method of claim 11, wherein step (d) proceeds by preferentially eliminating candidate solutions having different abundances of components than the heparin-like glycosaminoglycan mixture of interest before eliminating candidate solutions having the same abundances of components as the heparin-like glycosaminoglycan mixture of interest but having different component compositions.

13. The method of claim 12, wherein step (d) proceeds by preferentially eliminating candidate solutions having different component compositions than the heparin-like glycosaminoglycan mixture of interest before eliminating candidate solutions having the same component compositions as the heparin-like glycosaminoglycan mixture of interest but having different primary unit arrangements.

14. The method of claim 10, further comprising the step of computing a measure of difference between at least two of the candidate solutions remaining in the solution space following an elimination.

15. The method of claim 14, wherein step (d) comprises eliminating candidate solutions in a step-wise manner until the measure of difference is below a predetermined threshold.

16. The method of claim 14, wherein the measure of difference indicates a difference in biological activity.

17. The method of claim 14, wherein the step of computing a measure of difference comprises: (i) ordering the components of the at least two candidate solutions to identify analogous components; (ii) evaluating a first distance metric that accounts for a difference between the quantity of components of the at least two candidate solutions and a difference between the abundance of the analogous components of the at least two candidate solutions; (iii) evaluating a second distance metric that accounts for a difference between the composition of the analogous components of the at least two candidate solutions; (iv) evaluating a third distance metric that accounts for a difference between the arrangement of the primary units of the analogous components; and (v) computing the measure of difference using the first distance metric, the second distance metric, and the third distance metric.

18. The method of claim 14, wherein step (d) further comprises using the measure of difference to suggest an attribute of the heparin-like glycosaminoglycan mixture of interest to provide in a subsequent elimination step.

19. The method of claim 8, wherein in step (c), determining a value of the first attribute for a candidate solution comprises evaluating a model that predicts the first attribute for a mixture characterized by the candidate solution.

20. The method of claim 8, wherein in step (c), determining a value of the first attribute for a candidate solution comprises obtaining a value of the first attribute from a database.

21. The method of claim 8, wherein the heparin-like glycosaminoglycan mixture of interest comprises at least one biopolymer.

22. The method of claim 21, wherein the set of primary units comprises a plurality of disaccharide units.

23. The method of claim 8, wherein the set of primary units comprises at least one member selected from the group consisting of a monosaccharide, a disaccharide, and an oligosaccharide.

24. The method of claim 8, wherein the known set of primary units comprises more than 4 primary units.

25. The method of claim 8, wherein the known set of primary units comprises more than 20 primary units.

26. The method of claim 8, further comprising the step of identifying the set of primary units.

27. A method of characterizing a biological preparation comprising a plurality of heparin-like glycosaminoglycans, the method comprising the steps of: (a) generating a solution space comprising a plurality of candidate solutions, wherein each candidate solution is characterized by a quantity of components, and wherein each component is characterized by (i) an abundance of the component in the candidate solution, (ii) a composition defined by one or more members of a set of primary units, and (iii) an arrangement of the one or more primary units in the component; and (b) characterizing a biological preparation comprising a plurality of heparin-like glycosaminoglycans at least in part by eliminating candidate solutions from the solution space in a step-wise manner according to a comparison between an experimental measurement of each of a plurality of attributes of the biological preparation and a value of the respective attribute determined for each of at least a subset of the remaining candidate solutions in the solution space.

28. The method of claim 27, wherein the biological preparation is a pharmaceutical preparation.

29. The method of claim 27, wherein the method further comprises the step of: (c) producing a composition that is defined by at least one of the remaining candidate solutions in the solution space following step (b).

30. The method of claim 29, wherein the composition produced in step (c) is a bio-equivalent of the biological preparation.

31. The method of claim 29, wherein the method further comprises the step of: (d) characterizing the composition by performing a step-wise candidate elimination procedure.

32. A method for determining a measure of difference between at least two heparin-like glycosaminoglycan mixtures, the method comprising the steps of: (a) describing each of at least two heparin-like glycosaminoglycan mixtures having known components, wherein each component of each mixture is characterized by (i) an abundance of the component in the candidate mixture, (ii) a composition defined by one or more members of a set of primary units, and (iii) an arrangement of the one or more primary units in the component; (b) ordering the components of each of the at least two mixtures to identify analogous components; (c) evaluating a first distance metric that accounts for a difference between the quantity of components of the at least two mixtures and a difference between the abundance of analogous components of the at least two mixtures; (d) evaluating a second distance metric that accounts for a difference between the composition of analogous components of the at least two mixtures; (e) evaluating a third distance metric that accounts for a difference between the arrangement of the primary units of the analogous components; and (f) determining a measure of difference using the first distance metric, the second distance metric, and the third distance metric.

33. The method of claim 32, wherein the step of determining the measure of difference comprises using a predetermined functional relationship between the first, second, and third distance metrics.

34. The method of claim 33, wherein the predetermined functional relationship is a weighted sum of the first, second, and third distance metrics.

35. The method of claim 33, further comprising the step of determining the functional relationship by relating experimental measurements indicating biological activity to at least one of the first, second, and third distance metrics.

36. The method of claim 32, wherein the measure of difference indicates a difference in biological activity.

37. The method of claim 32, wherein the measure of difference indicates whether one mixture is bioequivalent of the other mixture.

38. A system for characterizing a heparin-like glycosaminoglycan mixture of interest, the system comprising: (a) a candidate generation module that generates a solution space comprising a plurality of candidate solutions; (b) a computation module that determines for each of at least a subset of the candidate solutions a value of a first attribute; (c) a comparison module that determines for each of the candidate solutions in (b) whether the value of the first attribute for the candidate matches an experimentally-measured value of the first attribute for a heparin-like glycosaminoglycan mixture of interest; and (d) an elimination module that eliminates at least one of the candidate solutions from the solution space whose first attribute value does not match the experimentally-measured value.

39. An apparatus for characterizing a heparin-like glycosaminoglycan mixture of interest, the apparatus comprising: (a) a memory for storing code that defines a set of instructions; and (b) a processor adapted to execute the set of instructions to: (i) generate a solution space comprising a plurality of candidate solutions; (ii) determine for each of at least a subset of the candidate solutions a value of a first attribute; (iii) determine for each of the candidate solutions in (ii) whether the value of the first attribute for the candidate matches an experimentally-measured value of the first attribute for a heparin-like glycosaminoglycan mixture of interest; and (iv) eliminate at least one of the candidate solutions from the solution space whose first attribute value does not match the experimentally-measured value.

* * * * *